US009867867B2

(12) United States Patent
Koistinaho et al.

(10) Patent No.: US 9,867,867 B2
(45) Date of Patent: Jan. 16, 2018

(54) IL-33 AND TREATMENT OF NEURODEGENERATIVE DISEASES

(71) Applicant: MAGIC EPOCH HOLDINGS LIMITED, Monaco (MC)

(72) Inventors: Jari Koistinaho, Leppävirta (FI); Tarja Malm, Siilinjärvi (FI); Eveliina Pollari, Kuopio (FI); Katja Kanninen, Kuopio (FI)

(73) Assignee: MAGIC EPOCH HOLDINGS LIMITED, Monaco (MC)

( * ) Notice: Subject to any disclaimer, the term of this patent is extended or adjusted under 35 U.S.C. 154(b) by 0 days.

(21) Appl. No.: 14/769,150

(22) PCT Filed: Feb. 21, 2014

(86) PCT No.: PCT/EP2014/053414
§ 371 (c)(1),
(2) Date: Aug. 20, 2015

(87) PCT Pub. No.: WO2014/128254
PCT Pub. Date: Aug. 28, 2014

(65) Prior Publication Data
US 2016/0000876 A1 Jan. 7, 2016

Related U.S. Application Data

(60) Provisional application No. 61/767,962, filed on Feb. 22, 2013.

(30) Foreign Application Priority Data

Feb. 22, 2013 (FI) ...................... 20135169

(51) Int. Cl.
*A61K 38/20* (2006.01)
(52) U.S. Cl.
CPC .................... *A61K 38/20* (2013.01)
(58) Field of Classification Search
None
See application file for complete search history.

(56) References Cited

U.S. PATENT DOCUMENTS

| 8,147,817 B2 | 4/2012 | Lee | |
|---|---|---|---|
| 2005/0203046 A1* | 9/2005 | Schmitz | C07K 16/244 514/44 A |
| 2008/0003199 A1* | 1/2008 | Lee | A61K 38/20 424/85.2 |

FOREIGN PATENT DOCUMENTS

| WO | 2005/079844 A2 | 9/2005 |
| WO | 2007/130627 A2 | 11/2007 |
| WO | 2009/053098 A1 | 4/2009 |
| WO | 2012145209 A2 | 10/2012 |

OTHER PUBLICATIONS

Onda et al., J Cereb Blood Flow Metab, Nov. 1999, vol. 19 No. 11:1279-1288.*
Kurowska-Stolarska, et al, IL-33 induces antigen-specific IL-5+ T cells and promotes allergic-induced airway inflammation independent of IL-4, J Immunol, 181 pp. 4780-4790, 2008.*
Hu, et al., "Microglia/Macrophage Polarization Dynamics Reveal Novel Mechanism of Injury Expansion After Focal Cerebral Ischemia," Stroke, Nov. 2012, DOI: 10.1161/STROKEAHA.112.659656.
Ma, et al., "Regulation of macrophage activation," CMLS, Cell. Mol. Life Sci. 60 (2003) 2334-2346.
Kanninen, et al., "Nuclear factor erythroid 2-related factor 2 protects against beta amyloid," Molecular and Cellular Neuroscience 39 (2008) 302-313.
Malm, et al., "Bone-marrow-derived cells contribute to the recruitment of microglial cells in response to β-amyloid deposition in APP/PS1 double transgenic Alzheimer mice," Neurobiology of Disease 18 (2005) 134-142.
Miller, et al., "IL-33 reduces the development of atherosclerosis," The Journal of Experimental Medicine vol. 205, No. 2, 339-346, Feb. 18, 2008.
Schwartz, Michal, "'Tissue-repairing' blood-derived macrophages are essential for healing of the injured spinal cord: From skin-activated macrophages to infiltrating blood-derived cells," Brain, Behavior, and Immunity 24, 1054-1057 (2010).
McPherson, et al., "In vivo molecular markers for pro-inflammatory cytokine M1 stage and resident microglia in trimethyltin-induced hippocampal injury," Neurotox Res. Jan. 2014; 25(1): doi:10.1007/s12640-013-9422-3.
Nishi, et al., "Behavioral, Histological, and Ex Vivo Magnetic Resonance Imaging Assessment of Graded Contusion Spinal Cord Injury in Mice," Journal of Neurotrauma, vol. 24, No. 4, (2007).
National Board of Patent and Registration Search Report in Finnish Patent Application No. 20135169, dated Oct. 17, 2013.
Yasuoka, et al., "Production and functions of IL-33 in the central nervous system," Brain Research 1385 (2011) 8-17.

(Continued)

*Primary Examiner* — Kimberly A. Ballard
*Assistant Examiner* — Stacey MacFarlane
(74) *Attorney, Agent, or Firm* — Foley & Lardner LLP

(57) ABSTRACT

The present invention relates to the fields of life sciences and medicine. Specifically, the invention relates to therapies of neurodegenerative diseases. More specifically, the present invention relates to interleukin-33 (IL-33), a fragment thereof, a polynucleotide encoding IL-33 or a fragment thereof for use in treatment or prevention of a neurodegenerative disease involving inflammation in a subject and to a method of treating or preventing a neurodegenerative disease involving neuroinflammation in a subject. Still, the present invention relates to IL-33, a fragment thereof, a polynucleotide encoding IL-33 or a fragment thereof for use in improving or restoring neuronal function or endogenous neuronal repair mechanisms, or enhancing endogenous neurogenesis, oligodendrogenesis or neuronal differentiation in a subject. Also, the present invention relates to a method of improving or restoring neuronal function or endogenous neuronal repair mechanisms, or enhancing endogenous neurogenesis, oligodendrogenesis or neuronal differentiation in a subject.

6 Claims, 22 Drawing Sheets

(56) References Cited

OTHER PUBLICATIONS

Miana-Mena, et al., "Optimal methods to characterize the G93A mouse model of ALS," Amyotrophic Lateral Sclerosis. 2005; 6:55-62, (2005).
Shuaib, et al., "Effects of Nonpeptide V1 Vasopressin Receptor Antagonist SR-49059 on Infarction Volume and Recovery of Function in a Focal Embolic Stroke Model," Stroke, Dec. 2002, DOI: 10.1161/01. STR.0000039405.31526.06 (2002).
Montagne, et al., "Ultra-sensitive molecular MRI of cerebrovascular cell activation enables early detection of chronic central nervous system disorders," NeuroImage 63 (2012) 760-770.
Pollari, et al., "Granulocyte colony stimulating factor attenuates inflammation in a mouse model of amyotrophic latearl sclerosis," Journal of Neuroinflammation 2011, 8:74, (2011).
Yoshimura, et al., "Post-ischemic inflammation in the brain," Frontiers in Immunology | Inflammation, vol. 3, Article 132, May 2012.
Busch, et al., "Overcoming Macrophage-Mediated Axonal Dieback Following CNS Injury," The Journal of Neuroscience, 29(32):9967-9976, Aug. 12, 2009.
Cassetta, et al., "Macrophage Polarization in Health and Disease," TheScientificWorldJOURNAL (2011) 11, 2391-2402.
Bouet, et al., "The adhesive removal test: a sensitive method to assess sensorimotor deficits in mice," Nature Protocols, vol. 4, No. 10, 1560-1564 (2009).
Chen, et al., "Inflammation & apoptosis in spinal cord injury," Indian J. Med. Res. 135, Mar. 2012, pp. 287-296.
Christophi, et al., "Interleukin-33 upregulation in peripheral leukocytes and CNS of multiple sclerosis patients," Clinical Immunology (2012) 142, 308-319.
Accession No. AAX86998, interleukin-33 [*Homo sapiens*], http://www.ncbi.nlm.nih.gov/protein/AAX86998.1, retrieved Nov. 10, 2013.
Written Opinion of the International Searching Authority for International Application No. PCT/EP2014/053414, dated Aug. 28, 2014.
Shin, et al., "Alternatively Activated macrophages in Spinal Cord Injury and Remission: Another Mechanism for Repair?," Mol. Neurobiol (2013) 47:1011-1019.
Accession No. NM_033439, *Homo spaiens* chromosome 9 open reading frame 26 (NF-HEV) (C9orf26), mRNA, http://www.ncbi.nlm.nih.gov/nuccore/NM_033439 .1 , retrieved Nov. 15, 2013.
Basso, et al., "Basso Mouse Scale for Locomotion Detects Differences in Recovery after Spinal Cord Injury in Five Common Mouse Strains," Journal of Neurotrauma, vol. 23, No. 5, pp. 635-659, (2006).
Accession No. NM_033439.3, *Homo spaiens* interleukin 33 (IL33), transcript variant 1, mRNA, hhtp://nlm.nih.gov/nuccore/NM_033za9.3, retrieved Nov. 15, 2013.
Chapuis, et al., "Transcriptomic and genetic studies identify IL-33 as a candidate gene for Alzheimer's disease," Mol Psychiatry, Nov. 2009; 14(11): 1004-1016.
David, et al., "Repertoire of microglial and macrophage responses after spinal cord injury," Nature Reviews, Neuro, vol. 12, (Jul. 2011).
Jiang, et al., "IL-33 attenuates EAE by suppressing IL-17 and IFN-γ production and inducing alternatively activated macrophages," Eur. J. Immunol. 42:1804-1814, (2012).
Fumagalli, et al., "CX3CR1 Deficiency Induces an Early rotective Inflammatory Environment in Ischemic Mice," GLIA 2013;61:827-842.
Guerrero, et al., "Blockade of interleukin-6 signaling inhibits the classic pathway and promotes an alternative pathway of macrophage activation after spinal cord injury in mice," Journal of Neuroinflammation 2012, 9:40.
Jiang, et al., "Substance P induced M2-type macrophages after spinal cord injury," NeuroReport 2012, vol. 23, No. 13 (2012).
Kopra, et al., "A mouse model for Finnish variant late infantile neuronal ceroid lipofuscinosis, CLN5, reveals neuropathology associated with early aging," Human Molecular Genetics, vol. 13, No. 23, (2004).
Lin, et al., "Reduced levels of interleukin 33 and increased levels of soluble ST2 in subjects with amyotrophic lateral sclerosis," Journal of Neuroimmunology 249 (2012) 93-95.
Kigerl, et al., "Identification of Two Distinct Macrophage Subsets with Divergent Effects Causing either Neurotoxicity or Regeneration in the Injured Mouse Spinal Cord," The Journal of Neuroscience, 29(43):13435-13444, Oct. 28, 2009.
Communication issued on EP Application 14705537.0, dated Sep. 21, 2016.

* cited by examiner

A

B

C

D

```
Human  1   M P MKYSTNKIS AK  KN ASK A C--F  G SQQKAKEVCP YFM LRSGIMI KEAC
Mouse  1   M P MKYSNSKIS AK  SS AGEA VPPCK R SQQKTKE CH YCM LRSGITI KETS Human  59  YFR ETTKRPSLK GRKHKRHLVLAACQQQSTVECFAFG SG QK TRA HDSSITGISP
Mouse  61  YFR EPTKRYSLK GTKHEENFSAYPRDSR-----KRSL GS QA AAS DTLSIQGTSL Human  119  TEYLASLSTYNDQS  FALEDESYEIYV DLKKDEKKDKVLLSYYESQHPSNESGDGVD
Mouse  116  TQSPASLSTYNDQS  FVLENGCYVINV DSGKDQEQDQVLLRYYESPCPASQSGDGVD Human  179  GKMLMVT SPTKD--FWLHANNK HSVELH C KPLP QAFFVLHNMHSNCVSFECKTDP
Mouse  176  GKKLMVN SPIKDTDIWLHANDK YSVELQ G VSPP QAFFVLHKKSSDFVSFECKNLP Human  237  GV IGVKDNHLAL KVDSSENLCTENI FKLSET
Mouse  236  GT IGVKDNQLAL EEKDES---CNNI FKLSKI
```

Figure 9.

SEQUENCE LISTING

```
<160> NUMBER OF SEQ ID NOS: 4

<210> SEQ ID NO 1
<211> LENGTH: 270
<212> TYPE: PRT
<213> ORGANISM: Homo sapiens
<220> FEATURE:
<221> NAME/KEY: SOURCE
<222> LOCATION: 1..270
<223> OTHER INFORMATION: /mol_type="protein"
      /note="IL-33 UniProtKB O95760"
      /organism="Homo sapiens"

<400> SEQUENCE: 1

Met Lys Pro Lys Met Lys Tyr Ser Thr Asn Lys Ile Ser Thr Ala Lys
1               5                   10                  15

Trp Lys Asn Thr Ala Ser Lys Ala Leu Cys Phe Lys Leu Gly Lys Ser
            20                  25                  30

Gln Gln Lys Ala Lys Glu Val Cys Pro Met Tyr Phe Met Lys Leu Arg
        35                  40                  45

Ser Gly Leu Met Ile Lys Lys Glu Ala Cys Tyr Phe Arg Arg Glu Thr
    50                  55                  60

Thr Lys Arg Pro Ser Leu Lys Thr Gly Arg Lys His Lys Arg His Leu
65                  70                  75                  80

Val Leu Ala Ala Cys Gln Gln Gln Ser Thr Val Glu Cys Phe Ala Phe
                85                  90                  95

Gly Ile Ser Gly Val Gln Lys Tyr Thr Arg Ala Leu His Asp Ser Ser
            100                 105                 110

Ile Thr Gly Ile Ser Pro Ile Thr Glu Tyr Leu Ala Ser Leu Ser Thr
        115                 120                 125

Tyr Asn Asp Gln Ser Ile Thr Phe Ala Leu Glu Asp Glu Ser Tyr Glu
    130                 135                 140

Ile Tyr Val Glu Asp Leu Lys Lys Asp Glu Lys Lys Asp Lys Val Leu
145                 150                 155                 160

Leu Ser Tyr Tyr Glu Ser Gln His Pro Ser Asn Glu Ser Gly Asp Gly
                165                 170                 175

Val Asp Gly Lys Met Leu Met Val Thr Leu Ser Pro Thr Lys Asp Phe
```

```
                180                 185                 190
Trp Leu His Ala Asn Asn Lys Glu His Ser Val Glu Leu His Lys Cys
                    195                 200                 205

Glu Lys Pro Leu Pro Asp Gln Ala Phe Phe Val Leu His Asn Met His
            210                 215                 220

Ser Asn Cys Val Ser Phe Glu Cys Lys Thr Asp Pro Gly Val Phe Ile
225                 230                 235                 240

Gly Val Lys Asp Asn His Leu Ala Leu Ile Lys Val Asp Ser Ser Glu
                245                 250                 255

Asn Leu Cys Thr Glu Asn Ile Leu Phe Lys Leu Ser Glu Thr
            260                 265                 270

<210> SEQ ID NO 2
<211> LENGTH: 813
<212> TYPE: DNA
<213> ORGANISM: Homo sapiens
<220> FEATURE:
<221> NAME/KEY: source
<222> LOCATION: 1..813
<223> OTHER INFORMATION: /mol_type="other DNA"
      /note="IL-33 cDNA NM_033439"
      /organism="Homo sapiens"

<400> SEQUENCE: 2
atgaagccta aaatgaagta ttcaaccaac aaaatttcca cagcaaagtg gaagaacaca      60
gcaagcaaag ccttgtgttt caagctggga aaatcccaac agaaggccaa agaagtttgc     120
cccatgtact ttatgaagct ccgctctggc cttatgataa aaaaggaggc ctgttacttt     180
aggagagaaa ccaccaaaag gccttcactg aaaacaggta gaaagcacaa aagacatctg     240
gtactcgctg cctgtcaaca gcagtctact gtggagtgct ttgcctttgg tatatcaggg     300
gtccagaaat atactagagc acttcatgat tcaagtatca caggaatttc acctattaca     360
gagtatcttg cttctctaag cacatacaat gatcaatcca ttacttttgc tttggaggat     420
gaaagttatg agatatatgt tgaagacttg aaaaagatg aaaagaaaga taaggtgtta     480
ctgagttact atgagtctca acacccctca aatgaatcag gtgacggtgt tgatggtaag     540
atgttaatgg taaccctgag tcctacaaaa gacttctggt tgcatgccaa caacaaggaa     600
cactctgtgg agctccataa gtgtgaaaaa ccactgccag accaggcctt ctttgtcctt     660
cataatatgc actccaactg tgtttcattt gaatgcaaga ctgatcctgg agtgtttata     720
ggtgtaaagg ataatcatct tgctctgatt aaagtagact cttctgagaa tttgtgtact     780
gaaaatatct tgtttaagct ctctgaaact tag                                 813

<210> SEQ ID NO 3
<211> LENGTH: 266
<212> TYPE: PRT
<213> ORGANISM: Mus musculus
<220> FEATURE:
<221> NAME/KEY: SOURCE
<222> LOCATION: 1..266
<223> OTHER INFORMATION: /mol_type="protein"
      /note="IL-33 UniProtKB Q8BVZ5"
      /organism="Mus musculus"

<400> SEQUENCE: 3

Met Arg Pro Arg Met Lys Tyr Ser Asn Ser Lys Ile Ser Pro Ala Lys
1               5                   10                  15

Phe Ser Thr Ala Gly Glu Ala Leu Val Pro Pro Cys Lys Ile Arg
            20                  25                  30
```

Arg Ser Gln Gln Lys Thr Lys Glu Phe Cys His Val Tyr Cys Met Arg
 35                  40                  45

Leu Arg Ser Gly Leu Thr Ile Arg Lys Glu Thr Ser Tyr Phe Arg Lys
 50                  55                  60

Glu Pro Thr Lys Arg Tyr Ser Leu Lys Ser Gly Thr Lys His Glu Glu
 65                  70                  75                  80

Asn Phe Ser Ala Tyr Pro Arg Asp Ser Arg Lys Arg Ser Leu Leu Gly
                 85                  90                  95

Ser Ile Gln Ala Phe Ala Ala Ser Val Asp Thr Leu Ser Ile Gln Gly
            100                 105                 110

Thr Ser Leu Leu Thr Gln Ser Pro Ala Ser Leu Ser Thr Tyr Asn Asp
        115                 120                 125

Gln Ser Val Ser Phe Val Leu Glu Asn Gly Cys Tyr Val Ile Asn Val
    130                 135                 140

Asp Asp Ser Gly Lys Asp Gln Glu Gln Asp Gln Val Leu Leu Arg Tyr
145                 150                 155                 160

Tyr Glu Ser Pro Cys Pro Ala Ser Gln Ser Gly Asp Gly Val Asp Gly
                165                 170                 175

Lys Lys Leu Met Val Asn Met Ser Pro Ile Lys Asp Thr Asp Ile Trp
            180                 185                 190

Leu His Ala Asn Asp Lys Asp Tyr Ser Val Glu Leu Gln Arg Gly Asp
        195                 200                 205

Val Ser Pro Pro Glu Gln Ala Phe Phe Val Leu His Lys Lys Ser Ser
    210                 215                 220

Asp Phe Val Ser Phe Glu Cys Lys Asn Leu Pro Gly Thr Tyr Ile Gly
225                 230                 235                 240

Val Lys Asp Asn Gln Leu Ala Leu Val Glu Glu Lys Asp Glu Ser Cys
                245                 250                 255

Asn Asn Ile Met Phe Lys Leu Ser Lys Ile
            260                 265

<210> SEQ ID NO 4
<211> LENGTH: 801
<212> TYPE: DNA
<213> ORGANISM: Mus musculus
<220> FEATURE:
<221> NAME/KEY: source
<222> LOCATION: 1..801
<223> OTHER INFORMATION: /mol_type="other DNA"
      /note="IL-33 cDNA NM_133775"
      /organism="Mus musculus"

<400> SEQUENCE: 4
atgagaccta gaatgaagta ttccaactcc aagatttccc cggcaaagtt cagcagcacc      60
gcaggcgaag ccctggtccc gccttgcaaa ataagaagat cccaacagaa gaccaaagaa     120
ttctgccatg tctactgcat gagactccgt tctggcctca ccataagaaa ggagactagt     180
tattttagga agaacccac gaaaagatat tcactaaaat cgggtaccaa gcatgaagag      240
aacttctctg cctatccacg ggattctagg aagagatcct tgcttggcag tatccaagca     300
tttgctgcgt ctgttgacac attgagcatc caaggaactt cacttttaac acagtctcct     360
gcctccctga gtacatacaa tgaccaatct gttagttttg ttttggagaa tggatgttat     420
gtgatcaatg ttgacgactc tggaaaagac caagagcaag accaggtgct actacgctac     480
tatgagtctc cctgtcctgc aagtcaatca ggcgacggtg tggatgggaa gaagctgatg     540
gtgaacatga gtcccatcaa agacacagac atctggctgc atgccaacga caaggactac     600

-continued

```
tccgtggagc ttcaaagggg tgacgtctcg cctccggaac aggccttctt cgtccttcac    660
aaaaagtcct cggactttgt ttcatttgaa tgcaagaatc ttcctggcac ttacatagga    720
gtaaaagata accagctggc tctagtggag gagaaagatg agagctgcaa caatattatg    780
tttaagctct cgaaaatcta a                                              801
```

IL-33 AND TREATMENT OF NEURODEGENERATIVE DISEASES

This application is a national application of PCT-application number PCT/EP2014/053414 filed on Feb. 21, 2014, which claims priority of the US provisional application number 61/797,962 and the Finnish national application number FI20135169 both of which were filed on Feb. 22, 2013, and all of which are incorporated herein by reference.

FIELD OF THE INVENTION

The present invention relates to the fields of life sciences and medicine. Specifically, the invention relates to therapies of neurodegenerative diseases. More specifically, the present invention relates to interleukin-33 (IL-33), a fragment thereof, a polynucleotide encoding IL-33 or a fragment thereof for use in treatment or prevention of a neurodegenerative disease involving inflammation in a subject and to a method of treating or preventing a neurodegenerative disease involving neuroinflammation in a subject. Still, the present invention relates to IL-33, a fragment thereof, a polynucleotide encoding IL-33 or a fragment thereof for use in improving or restoring neuronal function or endogenous neuronal repair mechanisms, or enhancing endogenous neurogenesis, oligodendrogenesis or neuronal differentiation in a subject. Also, the present invention relates to a method of improving or restoring neuronal function or endogenous neuronal repair mechanisms, or enhancing endogenous neurogenesis, oligodendrogenesis or neuronal differentiation in a subject.

BACKGROUND OF THE INVENTION

Neurodegeneration means progressive loss of structure or function of neurons, including death of neurons. Neurons are the building blocks of the nervous system which includes the brain and spinal cord. Neurons normally don't reproduce or replace themselves, so when they become damaged or die they cannot be replaced by the body. Examples of neurodegenerative diseases include Parkinson's, Alzheimer's, Huntington's disease, spinal cord injury, stroke and amyotrophic lateral sclerosis.

Neurodegenerative diseases are incurable and debilitating conditions that result in progressive degeneration and/or death of nerve cells. This causes problems with movement (called ataxias), or mental functioning (called dementias). Many neurodegenerative diseases are caused by traumas directed at brain or spinal cord, or either hereditary or sporadic genetic mutations. The greatest risk factor for neurodegenerative diseases is aging.

Inflammation is a defense reaction against diverse insults, designed to remove noxious agents and to inhibit their detrimental effects. It consists of molecular and cellular mechanisms and an intricate network of controls to keep them in check. In neurodegenerative diseases, inflammation may be triggered by the accumulation of aggregated or otherwise modified proteins, by signals emanating from injured neurons, or by imbalances between pro- and anti-inflammatory processes.

Spinal Cord Injury

Spinal cord injury (SCI) is classified as damage to the spinal cord caused by trauma, instead of disease, with symptoms ranging from pain to paralysis to incontinence. Any injury that involves the head, pelvic fractures, penetrating injuries in the area of the spine or injuries that result due to a fall from height, may result in spinal cord damage. The most common causes of SCI are motor vehicle accidents, falls and violence.

In the US, there are an estimated 12,000 new cases of SCI each year, with approximately 260,000 individuals afflicted by SCI. In Europe, there are estimated to be roughly 9,000 new SCI cases per year. Most incidences of SCI occur in people between the ages of 16-30 and hence healthcare expenses can be considerable, varying depending upon the severity of injury. Estimated lifetime costs for a tetraplegic patient are greater than a $1,000,000. These figures do not include any indirect costs, such as losses in salary, which are estimated to be approximately $64,000 per year.

Treatment options for SCI are extremely limited, with physical therapy a major treatment modality. Methylprednisolone, which helps to reduce swelling in the spinal cord, is widely prescribed as an off-label drug, but does not serve most patients needs. There are currently no therapies to alleviate, or repair, the incurred damage to the spinal cord. Very few compounds are in late stage development with the limited examples including Lyrica (a calcium channel modulator, targets neuropathic pain), umbilical cord blood mononuclear cell transplants (aimed at improving functional recovery) and Procord (autologous activated macrophage therapy, aimed at facilitating neuroprotection and wound healing). However, none of these molecules are expected to reach the market before 2017.

Amyotrophic Lateral Sclerosis

Amyotrophic lateral sclerosis (ALS), also referred to as motor neuron disease and Lou Gehrig's disease, is the most common form of the motor neuron diseases. The disorder is characterised by rapidly progressive weakness, muscle atrophy, twitching and spasticity, difficulty with speaking and swallowing and a decline in breathing ability. The defining feature of ALS is the death of both upper and lower motor neurons in the motor cortex of the brain, the brain stem, and the spinal cord. The disease has its onset usually in midlife and leads to death within 3-5 years from diagnosis, usually due to respiratory failure. Once diagnosed, only 10% of patients survive for longer than 10 years. In the US, there are approximately 30,000 ALS sufferers, with 5,000 new cases each year.

There is no curative therapy for ALS and palliative care remains the most important means of treatment. Riluzole is currently the only treatment found to improve survival, by 3-5 months, but patients do not report any subjective improvement. The mechanism of riluzole action is a matter of debate and was originally proposed to act as a sodium channel blocker, associated with damaged neurons, so reducing the influx of calcium ions and indirectly preventing the stimulation of glutamate receptors. However, no binding of riluzole to any receptor has been shown and its anti-glutamate action is still detectable in the presence of sodium channel blockers.

There are currently several ongoing clinical trials for novel ALS treatments. Dexpramipexole has been shown to improve mitochondrial function and to confer significant cellular protection in neurons under stress. A Phase II clinical trial, of dexpramipexole, showed a slowing of ALS disease progression, with a Phase III trial now initiated. Edaravone, a free radical scavenger, is currently in Phase III trial for ALS, with initial results suggesting a slowing in disease progression.

Stroke

Stroke is the rapid loss of brain function due to a disturbance in the blood supply to the brain. This may be caused by a blockage (ischemic stroke) or by a rupture to a blood vessel or an abnormal vasculature (hemorrhagic). Approximately 87% of strokes are caused by ischemia and the remainder by hemorrhage. Stroke is currently the second leading cause of death in the Western world, after heart disease and before cancer, causing ~10% of deaths worldwide. Stroke can affect patients physically, mentally and emotionally, the extent of which is dependent upon the size and location of the lesion. Disability affects 75% of stroke patients enough to decrease their employability. Physical disabilities can include muscle weakness, numbness, speech and vision loss. Post-stroke emotional disabilities include anxiety, panic attacks, apathy and psychosis. Depression is also commonly reported, affecting 30-50% of stroke survivors.

Immediate treatment for stroke is dependent upon the cause (ischemic or hemorrhagic) and may require surgery, for example, to remove a blood clot or to repair a bleed. To date, the only clinically approved therapy for stroke is treatment with recombinant tissue plasminogen activator (tPA) and other drugs, such as dipyridamole and clopidogrel may be used only in the secondary prevention of stroke in patients with previous history of ischemic events. However tPA treatment must be provided within a limited timeframe after stroke onset and novel strategies are required for neuroprotection rather than clot dissolution. The major disadvantage of tPA therapy is the increased incidence of hemorrhagic transformation and thus only a fraction of patients, approximately 5% are suitable for receiving tPA therapy. Rehabilitation, to regain and relearn skills, is typically required by most stroke patients and usually involves a multidisciplinary team with activities such as physical, occupational and speech therapy. For those stroke sufferers who have been severely affected, nursing care may also be required to provide, for example, feeding, hydration and body positioning.

There remains a significant unmet need for effective and specific therapies delaying and alleviating the symptoms of neurodegenerative diseases.

Neuronal Ceroid Lipofuscinoses

Neuronal ceroid lipofuscinoses (NGLs) are the most common group of neurodegenerative diseases affecting children, with an incidence of up to 1:12500. There are at least eight different childhood forms of NCL, distinguished by the age of onset and the genetic defect, and three adult disease forms. The exact physiological functions of the NCL proteins remain unclear.

Neuroinflammation is an early change in NCL affected animals and humans and it is believed that this is likely to have a substantial role in subsequent neuronal cell loss. Aggregates form in the lysosomes in all NCL forms. Neuronal degeneration and glial activation lead to motor dysfunction, cognitive dysfunction and seizures. There is no effective treatment or cure for the NCLs.

The function of the protein encoding the Cln5 gene, causative of the CLN5 disease form of NCL, remains unknown. Cln5 mutations cause a variant late-infantile human disease and some cases of juvenile and adult clinical disease. Cln5 is a soluble protein located in the lysosomes.

BRIEF DESCRIPTION OF THE INVENTION

The objects of the invention are achieved by utilizing a molecule with surprising effects on neurodegenerative diseases. It has now been found that IL-33 has a treating or preventive effect on subjects with neurodegenerative diseases. The present invention is based on the idea of providing IL-33 or any fragment thereof as a medicament for alleviating neurodegenerative symptoms of patients or curing the neurodegenerative disease. By the present invention it is possible to improve neural regenerative processes for example after the acute phase of the degenerative disease. Also, the present invention makes it possible to enhance endogenous neurogenesis, oligodendrogenesis or neuronal differentiation.

An object of the present invention is thus to provide a tool and a method for effective and specific treatment of neurodegenerative diseases involving neuroinflammation, especially SCI, ALS, stroke and neuronal ceroid lipofuscinoses. Thus, the present invention solves the problems of conventional unsuccessful and unspecific therapies. IL-33 is a natural molecule normally occurring in humans or animals and it has minor or no side effects on a treated subject. Induction of an immune reaction by IL-33 provides a simple and safe way to achieve higher levels of therapeutic efficacy. Treatment with IL-33 is peripheral and the peptide does not need to penetrate the blood brain barrier. Thus low dosages of IL-33 are enough to reach therapeutic efficacy.

The present invention is directed to IL-33, a fragment thereof, a polynucleotide encoding for IL-33 or a fragment thereof for use in treatment or prevention of a neurodegenerative disease involving neuroinflammation in a subject.

Also, the present invention is directed to a use of IL-33, a fragment thereof, a polynucleotide encoding for IL-33 or a fragment thereof in the manufacture of a medicament for treating or preventing a neurodegenerative disease involving neuroinflammation in a subject.

Still, the present invention is directed to IL-33, a fragment thereof, a polynucleotide encoding for IL-33 or a fragment thereof for use in improving or restoring neuronal function or endogenous neuronal repair mechanisms, or enhancing endogenous neurogenesis, oligodendrogenesis or neuronal differentiation in a subject with neurodegenerative disease involving neuroinflammation or in a subject after neurodegenerative disease involving neuroinflammation.

Still, the present invention is directed to a use of IL-33, a fragment thereof, a polynucleotide encoding for IL-33 or a fragment thereof in the manufacture of a medicament for improving or restoring neuronal function or endogenous neuronal repair mechanisms, or enhancing endogenous neurogenesis, oligodendrogenesis or neuronal differentiation in a subject with neurodegenerative disease involving neuroinflammation or in a subject after neurodegenerative disease involving neuroinflammation.

The present invention is further directed to a method of treating or preventing a neurodegenerative disease involving neuroinflammation in a subject, wherein the method comprises administration of IL-33, a fragment thereof, a polynucleotide encoding for IL-33 or a fragment thereof to the subject in need thereof.

The present invention is still further directed to a method of improving or restoring neuronal function or endogenous neuronal repair mechanisms or enhancing endogenous neurogenesis, oligodendrogenesis or neuronal differentiation in a subject with neurodegenerative disease involving neuroinflammation or in a subject after neurodegenerative disease involving neuroinflammation, wherein the method comprises administration of IL-33, a fragment thereof, a polynucleotide encoding for IL-33 or a fragment thereof to the subject in need thereof.

Other objects, details and advantages of the present invention will become apparent from the following drawings, detailed description and examples.

BRIEF DESCRIPTION OF THE DRAWINGS

FIG. 1C shows that IL-33 treatment improved the functional recovery after ischemic insult as measured by adhesive removal test starting at 5 days post injury (dpi) (B). * indicates p<0.05 and ** indicates p<0.01 (one way ANOVA with Bonferroni posthoc test). dpi stands for days post injury. The data are shown as mean±standard error of mean.

FIG. 9 shows the amino acid sequence alignment of human IL-33 and mouse IL-33.

DETAILED DESCRIPTION OF THE INVENTION

Neurodegenerative Diseases Involving Neuroinflammation

Figure 1A:
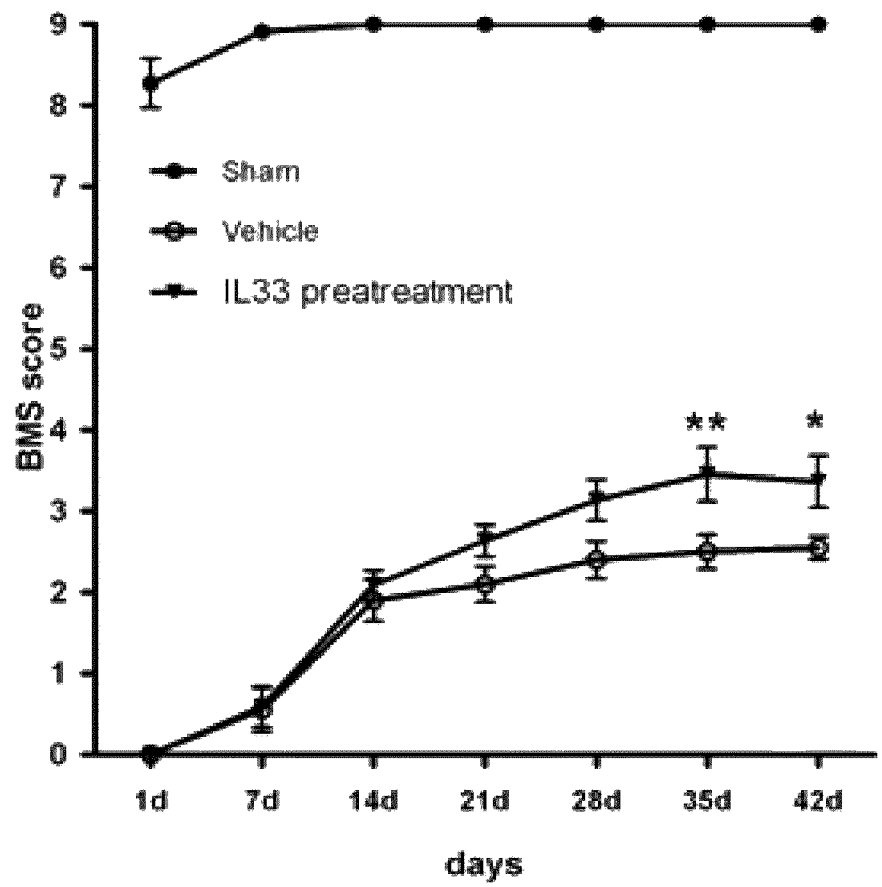
FIGS. 1A-C show that IL-33 ameliorates SCI induced motor deficits in C57BL/6j mice when given both (A) preand (B) post-injury. The improvement in Basso Mouse Scale (BMS) was greater when the treatment was started after the injury.
Figure 1B:
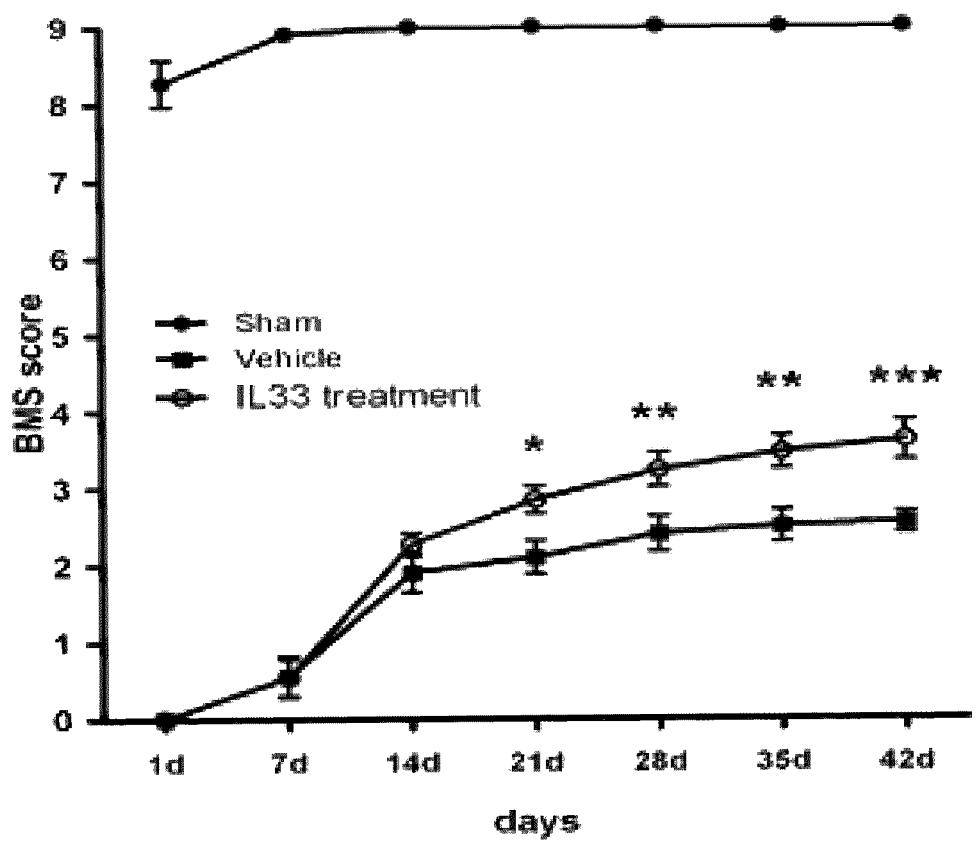

Neurodegeneration, either acute or slow and progressive dysfunction and loss of neurons and/or axons in the central nervous system, is the primary pathological feature of both acute and chronic neurodegenerative conditions. These diseases are also characterized by inflammatory responses, both innate and adaptive. Activation of the innate immune system is a crucial first line of defence, to opsonise and clear apoptotic cells. Furthermore, innate immune responses recruit cells of the adaptive immune system by secreting various cytokines and chemokines that induce adhesion molecules on the blood-brain barrier, and by inducing the expression of co-stimulatory molecules on microglia. Even though the initial aim of the immune activation is to protect the body from the initial insult, persistent inflammatory activation of the immune cells leads to neuronal damage.

As used herein, "a neurodegenerative disease involving neuroinflammation" refers to any neurodegenerative disease wherein innate and/or adaptive inflammatory response occurs. A neurodegenerative disease is either an acute or a chronic disease. Inflammation in neurodegenerative diseases is central or central and peripheral. In one embodiment of the invention a neurodegenerative disease involves both neuroinflammation and peripheral inflammation. As used herein, "neuroinflammation" refers to an activation of inflammatory mediator cells in the CNS. Peripheral inflammation can be detected by alterations in blood cytokine levels and leukocyte responses.

Immune responses have been shown in neurodegenerative disorders such as Alzheimer's disease (AD), Parkinson's disease, amyotrophic lateral sclerosis (ALS), paraneoplastic disorders, neurotropic viral infections, systemic lupus erythematous, traumatic brain injury (TBI), spinal cord injury (SCI), stroke, neuronal ceroid lipofuscinoses (NCL) and multiple sclerosis (MS). In one embodiment of the invention, a neurodegenerative disease involving neuroinflammation is selected from the group consisting of Alzheimer's disease (AD), Parkinson's disease, amyotrophic lateral sclerosis (ALS), paraneoplastic disorders, neurotropic viral infections, systemic lupus erythematous, traumatic brain injury (TBI), spinal cord injury (SCI), stroke, tauopathies, neuronal ceroid lipofuscinoses (NCL) and multiple sclerosis (MS). In another embodiment, a neurodegenerative disease involving neuroinflammation is selected from the group consisting of amyotrophic lateral sclerosis (ALS), spinal cord injury (SCI) and neuronal ceroid lipofuscinoses (NCL). In addition to there being no adequate therapies for SCI, ALS, NCL and stroke, they also share one prominent pathological feature: inflammation that occurs both centrally and peripherally.

In one specific embodiment of the invention the neurodegenerative disease involving neuroinflammation is ALS. In another specific embodiment of the invention the neurodegenerative disease involving neuroinflammation is SCI. In a further specific embodiment of the invention the neurodegenerative disease involving neuroinflammation is stroke. In a further specific embodiment of the invention the neurodegenerative disease involving neuroinflammation is NCL.

The therapeutic effect of the majority of conventional neuroprotectants aims to halt the acute phase of brain diseases (stroke, TBI, SCI etc), which starts at the onset of the injury and lasts for a few hours. The limiting factor with targeting the acute phase is time, since especially in sparse inhabited areas the "symptom to needle" time is often too long. When the acute phase is resolved, that is days to weeks after embolism, important processes of neuroregeneration and repair begin. The majority of the drugs in clinical trials for the treatment of brain diseases aim to target the acute phase and the vital recovery processes taking place weeks and even months after the insult are largely neglected. These processes include, but are not limited to, neurogenesis, oligodendrogenesis and formation of new neuronal connections. In addition, many pathways involved in neuronal death during the acute phase appear to be mandatory for repair processes in the resolution phase of the injury. This contradiction and poor knowledge of the factors regulating it's complexity have led to failure of neuroprotectants in clinical trials. The optimum treatment strategy for acute brain injuries is not only to attack the early, acute phase of neuronal death, but also to aim at improving the recovery and repair processes needed to compensate the function of lost neurons.

Macrophages are central players in the innate immune response following injury to CNS (David and Kroner, 2011). Exposure of macrophages to type 1 helper T cell (Th1) cytokines such as interferon gamma (IFN-γ) and tumor necrosis factor alpha (TNF-α) leads to their polarization to the M1 subpopulation (the classical, pro-inflammatory macrophages), which is associated with cytotoxic processes (Gordon, 2003; Ma et al., 2003; Kigerl et al., 2009; Busch et al., 2009; Cassetta et al., 2011; David and Kroner, 2011; Shechter and Schwartz, 2013) and correlates with the severity of the disease progression and tissue damage in SCI (David and Kroner, 2011). In contrast, the "alternatively activated" M2 macrophages demonstrate anti-inflammatory activities and are induced by type 2 helper T cell (Th2) cytokines such as interleukin (IL)-4, IL-10 and IL-13 (Gordon, 2003; Ma et al., 2003; Cassetta et al., 2011; Shechter and Schwartz, 2013). The M2 macrophages are essential in the amelioration of inflammation and facilitation of reparation after injuries such as SCI, stroke and TBI. Unfortunately, the microenvironment of the injured SC and brain favors M1 polarization and the appearance of M2 macrophages remains transient (Kigerl et al., 2009; Schwartz, 2010; David and Kroner, 2011; Shin et al., 2013).

In contrast to M1 type, M2 macrophages are involved in the recovery of SCI (Schwartz, 2010; David and Kroner, 2011; Guerrero et al., 2012) and are required for oligodendrocyte differentiation and therefore remyelination (Miron et al., 2013). The role and contribution of M2-type inflammation in the context of stroke is very similar to SCI. M2-type macrophages protect neurons from ischemic isults (Fumagalli et al., Hu et al.) and promote markers related to enhanced neurogenesis (Pherson et al.).

IL-33 based treatments of the present invention improve regenerative processes during or after a degenerative disease or a specific phase thereof. IL-33, a polynucleotide encoding IL-33 and/or fragments thereof support repair processes by inducing M2-shift in microglia activation. Indeed, IL-33 treatment enhances neuronal differentiation of neuronal precursor cells. Thus modification of the microenvironment of diseased brain to increase the number of M2 macrophages has beneficial effect through induction in pathways involved in neurorepair, such as but not limited to neurogenesis and oligodendrogenesis.

As used herein, "neuronal function" refers to any function of neurons including but not limited to neural connectivity. As used herein, "neural connectivity" refers to connections between neurons and interaction between neurons and glial cells. Neurons communicate with one another via synapses, where the axon terminal of one cell impinges upon another neuron's dendrite, soma or, less commonly, axon. Neurons can make connections even with tens of thousands of other cells. Synapses can be excitatory or inhibitory and either increase or decrease activity in the target neuron. Some neurons also communicate via electrical synapses, which are direct, electrically conductive junctions between cells. Improvement or restoration of neural connectivity alleviates symptoms of the degenerative disease in a patient.

As used herein, "endogenous neuronal repair mechanisms" refers to any mechanisms involved in demyelination, regulation of inflammation, axonal regeneration, neurogenesis, oligodendrogenesis, enhancement of neuronal function and health or restoration of neuronal connections and interaction between neurons and glial cells.

As used herein, "neuronal differentiation" refers to differentiation of neurons from stem cell precursors. The dividing stem cell precursors in the ventricular zone undergo a stereotyped pattern of cell movements as they progress through the mitotic cycle, leading to the formation of either new stem cells or postmitotic neuroblasts that differentiate into neurons. As cells become postmitotic, they leave the ventricular zone and migrate to their final positions in the developing brain. After migration immature neurons grow axons and dendrites. Synapses are generated between these axons and their postsynaptic partners.

As used herein "endogenous neurogenesis" refers to a process by which neurons are generated from neural stem cells and progenitor cells within a subject. By the present invention it is possible to modulate neurogenesis in the subventricular zone, in subgranular zone of the hippocampus or in any other region in peripheral or central nervous system where neurogenesis may take place.

As used herein "oligodendrogenesis" refers to the formation of oligodendrocytes. Oligodendrocytes are a type of neuroglia and their main function is to provide support and insulation to the axons in the central nervous system.

Spinal Cord Injury

SCI is caused by both primary and secondary injury mechanisms. The former relates more specifically to the actual mechanical damage that occurs at the type of trauma, such as shearing, tearing and stretching of axons, neurons and blood vessels. The latter, proceeds over minutes, hours, days and even months after the initial traumatic insult and can lead to significant expansion of the original damage, causing paralysis to extend to further segments. These secondary mechanisms are a consequence of delayed biochemical, metabolic and cellular changes, which are initiated by the primary injury, and includes inflammation, free radical induced cell death and glutamate excitotoxicity (Chen et al., 2010).

Neuroinflammation is a key component of secondary injury and plays a major role in regulating the pathogenesis of both acute and chronic SCI. Consequently, reduction of the inflammatory response, following SCI, could alleviate secondary degeneration and lead to a decrease in overall functional deficit.

Following SCI, central nervous system (CNS) inflammatory responses are initiated by both peripherally derived immune cells and activated glial cells that proliferate or migrate to the site of injury. Glial cells are major modulators of neuron viability and function. T cells play a crucial role in activating macrophages and mounting an immune response. Following access to the lesion site, lymphocytes can persist indefinitely, with T and B cell numbers shown to increase for at least 9 weeks in an SCI mouse model following trauma. Macrophages and microglia may participate in the inflammatory response through release of cytokines, such as TNF-$\alpha$, IL-1, IL-6, IL-10 and interferon, in addition to activation of specific interleukin receptors like IL-4R and IL-2R. Cytokine release can facilitate further CNS inflammatory responses by the induced expression of additional cytokines, chemokines, nitric oxide and reactive oxygen (Chen et al., 2010).

Amyotrophic Lateral Sclerosis

The majority of ALS cases are sporadic (sALS), meaning they occur without an inherited cause, and approximately 10% of cases are familial (fALS). The etiology of ALS is not clearly defined and hence the exact pathway to trigger the disease has remained obscure, complicating the development of efficient treatment. fALS cases have heterogenous genetic background and are caused by mutations in a range of genes. The most commonly affected genes include SOD1, FUS/TLS, TARDBP and C9ORF72. In addition to the complex background, the pathophysiological mechanisms in ALS are various and not completely understood. Glutamate excitotoxicity, mitochondrial dysfunction, oxidative stress and neuroinflammation are among the pathogenic cellular mechanisms that contribute to the neurodegeneration in ALS. The complexity of the disease is probably the underlying reason why development of treatments that could slow down the disease progression, or stop it, has been unsuccessful. Targeting treatments to individual pathogenic mechanisms has been inefficient and, therefore, medical interventions that can simultaneously affect several of the pathogenic mechanisms could provide an efficient therapy.

One of the most commonly mutated genes causing fALS is SOD1 (superoxide dismutase, a free radical scavenging enzyme), which accounts for 20% of cases. In addition, mutated SOD1 (mSOD1) has been identified in 1-3% of sALS cases. In 1993 the identification of mutated SOD1 as a cause for fALS, revolutionized the genetic research of ALS. From then, the list of known SOD1 mutations has expanded and in current knowledge there are almost 170 ALS-associated mutations in SOD1 at approximately 70 of the 153 amino acids, which are widely distributed throughout the gene.

The mechanism by which mutated SOD1 causes cellular toxicity and ALS is not fully understood. After identifying the connection between SOD1 mutations and fALS it was suggested by many researchers that disease onset was likely due to increased or decreased enzyme activity. These hypotheses were soon rejected due to the significant number of mutations distributed throughout the gene rather than localized to the active site. Secondly, it was discovered that the cause is not a loss of function, but rather a gain of toxic property, which is not dependent on SOD1 activity or aberrant protein aggregation. The loss of function theory is further disproved by mice that lack SOD1 gene and do not develop motoneuron disease. More importantly, several ALS patients with mSOD1 have normal levels of SOD1 activity.

Neuroinflammation is a hallmark of ALS and it manifests as activation of microglia and astrocytes in the CNS and is complimented by the involvement of peripheral immune cells. Astrocytes modulate synaptic transmission by regulating availability of several neurotransmitters and protect neurons from oxidative stress. Microglia are the immune effector cells of the CNS and depending on the surrounding factors they can be activated to anti- or pro-inflammatory direction. Both astrocytes and microglia can secrete neurotrophic factors to promote neuronal survival or under stress they can produce pro-inflammatory cytokines and other factors that are neurotoxic.

Involvement of inflammation in the CNS pathology of ALS is demonstrated by the activation and proliferation of microglia and infiltration of CD4 and CD8 T-cells and dendritic cells into the spinal cords of ALS patients and transgenic mSOD1 mice. Moreover, mSOD1 expressing astrocytes are prone to exhibit an activated pro-inflammatory state, proposing an elevated inflammatory status in ALS. In the CSF of ALS patients there are elevated levels of IL-6, monocyte chemoattractant protein-1, and IL-8, whereas in postmortem spinal cord samples pro-inflammatory prostaglandin E2 and cyclooxygenase-2 (Cox-2, an enzyme synthesizing inflammatory prostanoids) are elevated. Pro-inflammatory cytokines IL-1$\alpha$, IL-1$\beta$, and tumor necrosis factor-$\alpha$ (TNF-$\alpha$), in addition to Cox-2, are increased in mSOD1 mouse spinal cord. The immune response is also activated in the blood of ALS patients, where there is a reduction in regulatory T cells and monocytes already during the early stages of disease.

Stroke

Stroke can be either ischemic or hemorrhagic stroke. Post-ischemic neuroinflammation, following stoke, promotes brain swelling that ultimately leads to compression of normal brain tissue surrounding the ischemic core and the exacerbation of neurological defects.

Infiltrating immune cells, such as leukocytes, together with injured brain cells, such as astrocytes, promote ischemic brain inflammation by producing various inflammatory mediators. Macrophages and neutrophils are pivotal players in the various processes of brain inflammation whilst T or B lymphocytes have also been reported to participate in delayed brain inflammation.

As a result of infiltrating immune cells, various cytokines and mediators are produced. This includes IL-1$\beta$ and TNF-$\alpha$, which are expressed in the ischemic brain within 30 min and 1 hr respectively following stroke onset. IL-1$\beta$ enhances the expression of chemokines in microglia and astrocytes whilst TNF-α can promote leukocyte infiltration and blood brain barrier breakdown. IL-6 is also expressed in ischemic brain tissue although its role has not yet been established. Consistent with the above, TNF-α, IL-1 and IL-6 are found to be elevated in CSF and blood, in humans, following ischemic stroke.

The number of infiltrating immune cells reaches a peak by day 3 after stroke onset, with the majority of them being macrophages. Inflammatory cytokines, such as IL-1β, TNF-α, IL-23 and IL-12 have been shown to be produced from the macrophage and contribute to brain injury. T lymphocytes, considered to be neurotoxic effectors, have also been suggested to play a role in the delayed phase of brain ischemia, representing approximately 1-1.5% of all immune cells. These consist of 30–40% CD4+ helper T lymphocytes, 20–30% γδT lymphocytes and 20–30% CD8+ cytotoxic T lymphocytes. Depletion of CD4+ and CD8+T lymphocytes is reported to attenuate ischemic brain damage. T lymphocytes can produce various cytokines, such as IFN-γ and IL17. Although a protective effect by IFN-γ deficiency has yet to be observed, it is typically considered to be neurotoxic. IL-17 is most likely induced by IL-23, from infiltrating macrophages, with IL-17 KO mice showing significantly reduced ischemic brain damage. IL-17 is considered to be a promising therapeutic target for suppressing post-ischemic inflammation (Yoshimura et al., 2012).

Neuronal Ceroid Lipofuscinoses

Neuronal ceroid lipofuscinoses (NGLs) are a group of inherited, fatal diseases. Up to date over 360 mutations in eleven genes have been reported to cause NCL. Protein accumulation in the lysosomes is one defining feature of these disorders and extensive evidence implicates neuroinflammation in a causative role. It is unclear what the exact mechanisms leading to pathology are.

Given the large number of genes implicated in NCL disease there are several mouse models for NCL and naturally occurring ovine disease models. Neuronal loss in NCL is preceded by glial activation in both mouse and ovine disease models. Those brain areas which show early inflammation display the most pronounced neuronal loss. Glial activation occurs pre-natally, before neuron loss or lysosomal protein aggregation.

Several NCL mouse models display increased expression of pro-inflammatory cytokines, including TNF-α, interleukin-1β(IL-1β), and TGF-β, as well as increased astrocytosis in the brain. Moreover, blood brain barrier permeability is compromised, leading to the infiltration of pro-inflammatory mediators into the brain.

Interleukin-33

IL-33 is a recently identified member of the IL-1 family that possesses strong Th2 type immunomodulatory functions. Several tissues, such as stomach, lung, spinal cord, brain and skin, express IL-33 mRNA with levels varying depending on cell type and activation. Protein level expression is most pronounced in fibroblasts, epithelial cells and endothelial cells. In the CNS, IL-33 is produced by endothelial cells and astrocytes and occasionally by neurons, but not by microglia.

IL-33 binds to a heterodimeric receptor complex consisting of a membrane-bound form of ST2 and IL-1 R accessory protein (IL-1 RAcP). There are three splice variants of ST2, a secreted soluble form, a membrane-bound form and a variant form. The soluble isoform of ST2 is able to bind IL-33 and thus inhibit its binding to and signaling through the membrane-bound ST2 receptor. ST2 is expressed mainly on mast cells and on Th2 cells. In the CNS the receptor complex is expressed by astrocytes and microglia and possibly by neurons.

IL-33 has a complex effect on the immune response and can promote both Th1 and Th2 type responses. By binding to its receptor complex on the cell membrane, IL-33 activates nuclear factor κB (NF-κB) and MAP kinases that promote the Th2 type inflammatory response. Administration of IL-33 also induces the production of Th2-associated cytokines in several tissues including *thymus*, spleen, liver and lungs. In a mouse model, IL-33 was shown to play a protective role in the development of atherosclerosis via the induction of IL-5 and oxidised low-density lipoprotein antibodies (Miller et al. 2008).

Some diseases are induced or exacerbated by IL-33. Allergic inflammation is aggravated by IL-33 induced activation of basophils, whilst in rheumatoid arthritis, IL-33 promotes inflammation by inducing neutrophil migration. Expression of IL-33 is increased in the epidermis of clinical psoriatic lesions and skin inflammation is provoked by IL-33 induced activation of mast cells and neutrophils. In asthma patients, IL-33 expression is increased in the lung epithelial cells, whilst airway inflammation was induced, by IL-33, in a mouse model of asthma.

Furthermore, IL-33 is known to induce proliferation of microglia and to promote the expression of pro-inflammatory cytokines including IL-1β and TNF-α (Yasuoka et al. 2011). In support of this, IL-33 is upregulated in both the periphery and CNS of multiple sclerosis patients and has been implicated in the pathogenesis of the disease (Christophi et al, 2012).

Additionally, a polymorphism in the IL33 gene appears to modify the risk of AD and expression of IL-33 is decreased in the brains of AD patients. Overexpression of IL-33 decreased secretion of β-amyloid peptide and IL-33 enhances phagocytosis by microglia (Chapuis et al., 2009, Yasuoka et al., 2011).

In the present invention IL-33, a fragment thereof, a polynucleotide encoding IL-33 or a fragment thereof is for treatment or prevention of a neurodegenerative disease involving neuroinflammation. As used herein, "IL-33" refers to any kind of IL-33 polypeptide or any variant thereof having a function of IL-33. As used herein, "a fragment" refers to any part of IL-33 having a therapeutic effect. In one embodiment of the invention the fragment has a function of IL-33. In one embodiment of the invention the function of IL-33 or a fragment thereof is to improve the body's response to a disease. In another embodiment of the invention, the function is to bind to a heterodimeric receptor complex consisting of a membrane-bound form of ST2 and IL-1 R accessory protein (IL-1 RAcP). The IL-33 polypeptides or fragments thereof may be either naturally occurring or modified (e.g. recombinant) purified polypeptides.

In one embodiment of the invention, IL-33, a fragment thereof, a polynucleotide encoding for IL-33 or a fragment thereof is of a human origin, a mouse origin, a rodent origin, or any combination thereof, such as a human-mouse, human-rodent, mouse-rodent, human-mouse-rodent combination. Most preferably IL-33, a fragment thereof, a polynucleotide encoding for IL-33 or a fragment thereof is of a human or mouse origin. In a further embodiment of the invention IL-33, a fragment thereof, a polynucleotide encoding for IL-33 or a fragment thereof is a recombinant IL-33, a recombinant fragment thereof, a recombinant polynucleotide encoding for IL-33 or a recombinant fragment thereof. It is possible to use a human, non-human or recombinant IL-33 or polynucleotide encoding IL-33 for a human patient or a human, non-human or recombinant IL-33 or polynucleotide encoding IL-33 for an animal. IL-33 variants or IL-33 of different origins have effects in the correct host organism.

In one embodiment of the invention IL-33 comprises an amino acid sequence having at least 52% or at least 69% sequence identity with a sequence as set forth in SEQ ID NO: 1 or SEQ ID NO: 3. For example FIG. 9 reveals that IL-33 of different organisms are similar by showing the amino acid sequence alignment of human IL-33 and mouse IL-33. IL-33 of the present invention may have an amino acid sequence having at least 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 or 99% sequence identity with a sequence as set forth in SEQ ID NO: 1. On the other hand, IL-33 of the present invention may have an amino acid sequence having at least 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 or 99% sequence identity with a sequence as set forth in SEQ ID NO: 3.

Identity of any sequence compared to the sequence shown in the present invention refers to the identity of any sequence compared to the entire sequence shown in the present invention. Sequence identity may be determined for example by using BLAST (Basic Local Alignment Search Tools) or FASTA (FAST-All). In the searches, setting parameters "gap penalties" and "matrix" are typically selected as default.

In another embodiment of the invention IL-33 comprises an amino acid sequence as set forth in SEQ ID NO: 1 or SEQ ID NO: 3. An amino acid sequence of human IL-33 is also shown in FIG. 9. In a further embodiment IL-33 has an amino acid sequence as set forth in SEQ ID NO: 1 or SEQ ID NO: 3.

Polynucleotides encoding IL-33 or a fragment thereof may be targeted into selected target cells or tissues in a manner that enables expression thereof in a therapeutically effective amount. In accordance with the present invention, gene therapy may be used in a therapeutically effective amount in a subject with neurodegenerative disease involving neuroinflammation. IL-33 polynucleotides described above may be applied in the form of recombinant DNA, plasmids, or viral vectors. Methods of delivering polynucleotides are available in the art. IL-33 polynucleotides may be delivered as naked polynucleotides or incorporated into a viral vector under a suitable expression control sequence. Suitable viral vectors are readily available in the art and include, but are not limited to, retroviral vectors, such as lentivirus vectors, adeno-associated viral vectors, and adenoviral vectors. According to some embodiments a vector cannot replicate in a mammalian subject.

As used herein, "a polynucleotide encoding IL-33" refers to any polynucleotide, such as single or double-stranded DNA or RNA, comprising a nucleic acid sequence encoding an IL-33 polypeptide. Multiple IL-33 encoding polynucleotide sequences exist for IL-33 polypeptides, and any of these may be used in the present invention. In some embodiments of the invention, IL33 gene comprises or has a nucleotide sequence as set forth in SEQ ID NO: 2 or SEQ ID NO: 4.

An IL-33 polynucleotide may also comprise a suitable promoter and/or enhancer sequence for expression in the target cells, said sequence being operatively linked upstream of the coding sequence. If desired, the promoter may be an inducible promoter or a cell type specific promoter.

SEQ ID NO: 1 shows an amino acid sequence for human IL-33 (UniProtKB 095760). SEQ ID NO: 2 shows a cDNA nucleotide sequence for human IL-33 (NM_033439). SEQ ID NO: 3 shows an amino acid sequence for mouse IL-33 (UniProtKB Q8BVZ5). SEQ ID NO: 4 shows a cDNA nucleotide sequence for mouse IL-33 (NM_133775). The recombinant mouse IL-33 (BioLegend) used for the animal models of the present invention corresponds to amino acids Ser109-Ile266 of mouse IL-33. These amino acids correspond to amino acids Ser112-Thr270 of SEQ ID NO: 1.

Mouse IL-33 is known to have gene ID number 77125 (*Mus musculus*) and human IL-33 is known to have gene ID number 90865 (*Homo sapiens*).

Pharmaceutical Composition and Administration

According to the present invention IL-33, a fragment thereof, a polynucleotide encoding IL-33 or a fragment thereof can be used for the manufacture of a medicament for treatment or prevention of a neurodegenerative disease involving neuroinflammation.

As used herein, the term "treatment" or "treating" refers to administration of at least IL-33, a fragment thereof, a polynucleotide encoding IL-33 or a fragment thereof to a subject, preferably a mammal or human subject, for purposes which include not only complete cure but also amelioration or alleviation of disorders or symptoms related to a degenerative disease in question. Therapeutically effective amount of IL-33, a fragment thereof, a polynucleotide encoding IL-33 or a fragment thereof refers to an amount with which the harmful effects of a neurodegenerative disease involving neuroinflammation (e.g. ALS, SCI or NCL) are, at a minimum, ameliorated. The harmful effects of a neurodegenerative disease involving neuroinflammation include but are not limited to muscle weakness, muscle atrophy, twitching, spasticity, difficulty with speaking and swallowing, speech and vision loss, decline in breathing ability, numbness, anxiety, panic attacks, apathy, psychosis, depression, pain, paralysis or incontinence. The effects of IL-33 or a fragment thereof may be either short term or long term effects.

According to the present invention IL-33, a fragment thereof, a polynucleotide encoding IL-33 or a fragment thereof is administered to a subject as a pharmaceutical composition. A pharmaceutical composition of the invention comprises at least IL-33, a fragment thereof, a polynucleotide encoding IL-33 or a fragment thereof. In addition a pharmaceutical composition may also comprise any other therapeutically effective agents, any other agents, such as a pharmaceutically acceptable solvent, diluent, carrier, buffer, excipient, adjuvant, antiseptic, filling, stabilising or thickening agent, and/or any components normally found in corresponding products.

The pharmaceutical composition may be in any form, such as in a solid, semisolid or liquid form, suitable for administration. A formulation can be selected from a group consisting of, but not limited to, solutions, emulsions, suspensions, tablets, pellets and capsules.

The pharmaceutical compositions may be produced by any conventional processes known in the art.

Amounts and regimens for therapeutic administration of IL-33, a fragment thereof, a polynucleotide encoding IL-33 or a fragment thereof can be determined readily by those skilled in the clinical art of treating degenerative diseases. Generally, the dosage of the IL-33, a fragment thereof, a polynucleotide encoding IL-33 or a fragment thereof varies depending on multiple factors such as age, gender, other possible treatments, neurodegenerative disease in question and severity of the symptoms. For administration of IL-33 or a fragment thereof a typical dose is in the range of 0.001 to 50 mg/kg, more specifically in the range of 0.01 to 20 mg/kg or 0.01 to 10 mg/kg, most specifically 0.03 to 1 mg/kg. For instance, when viral vectors are to be used for gene or polynucleotide delivery, the vector is typically administered, optionally in a pharmaceutically acceptable carrier, in an amount of $10^7$ to $10^{13}$ viral particles, preferably in an amount of at least $10^9$ or at least $10^{10}$ viral particles.

The present invention is utilized for use in treatment or prevention of a neurodegenerative disease involving neuroinflammation in a subject and in a method of treating or preventing a neurodegenerative disease involving neuroinflammation in a subject.

In one embodiment of the invention a subject is a human or an animal. A subject is in need of a treatment or prevention of a neurodegenerative disease with IL-33, a fragment thereof, a polynucleotide encoding IL-33 or a fragment thereof. Most preferably a subject is a human patient suffering from a neurodegenerative disease involving neuroinflammation. Also any animal, such as a pet, domestic animal or production animal, suffering from a neurodegenerative disease involving neuroinflammation may be a subject of the present invention.

Before classifying a subject as suitable for the therapy of the present invention, the clinician may for example study any symptoms or assay any disease markers of the subject. Based on the results deviating from the normal, the clinician may suggest IL-33 based treatment of the present invention for the subject.

Any conventional method may be used for administration of IL-33, a polynucleotide of fragments thereof or a pharmaceutical composition to a subject. The route of administration depends on the formulation or form of the composition, the disease, the patient, and other factors. In one embodiment of the invention, the administration is conducted through an intramuscular, intraarterial, intravenous, intracavitary, intracranial or intraperitoneal injection, or an oral administration.

Additionally, the administration of the IL-33, a polynucleotide or a fragment thereof can be combined to the administration of other therapeutic agents. The administration can be simultaneous, separate or sequential. The administration of IL-33, a polynucleotide or a fragment thereof can also be combined to other forms of therapy, such as surgery, and may be more effective than either one alone.

A desired dosage can be administered in one or more doses at suitable intervals to obtain the desired results. Only one administration of IL-33, a polynucleotide or a fragment thereof may have therapeutic effects, but specific embodiments of the invention require several administrations during the treatment period. For example, administration may take place from 1 to 30 times, 1 to 20 times, 1 to 10 times, two to eight times or two to five times in the first 2 weeks, 4 weeks, monthly or during the treatment period. The length of the treatment period may vary, and may, for example, last from a single administration to 1-12 months, two to five years or even more.

Any method or use of the invention may be executed either in vivo, ex vivo or in vitro.

It will be obvious to a person skilled in the art that, as the technology advances, the inventive concept can be implemented in various ways. The invention and its embodiments are not limited to the examples described below but may vary within the scope of the claims.

EXAMPLES

Materials and Methods
Spinal Cord Injury Model

Female, 10-12 weeks old C57BL/6J (Jackson Laboratories) mice were bred in the National Laboratory Animal Centre, University of Eastern Finland. The mice were housed in groups of three in cages under 12-hour light/dark cycle with water and standard rodent chow provided ad libitum. Additional water and powdered food was made available for the first 7 days after SCI. The experimental procedures were approved by the Animal Experiment Committee in State Provincial Office of Southern Finland and conducted according to the national regulation of the usage and welfare of laboratory animals. The mice were anesthetized with 5% isoflurane in 30% $O_2$/70% $N_2O$ and maintained in surgical depth anesthesia with 1%-1.5% isoflurane delivered through a nose mask during the operation. For the surgery the mice were placed on a controlled heating blanket to maintain body temperature at the constant level of 37±1° C. Moderate contusion SCI (60 kDynes force) was performed using an Infinite Horizons Impactor (Precision Scientific Intrumentation, Lexington, Ky.) as described in Pomeshchik et al., 2013. Mice that underwent laminectomy without impact served as sham controls.

ALS Transgenic Mice

Transgenic (TG) G93A-SOD1 mice (B6.Cg-Tg-(SOD1-G93A)1Gur/J, The Jackson Laboratory, Bar Harbot, Me., USA) with a high copy number of human G93A-SOD1 gene were maintained on C57B1/6J congenic background. Motor deficits and progressive paralysis start in these hemizygous mice at the age of 17-19 weeks and the end stage of the disease manifests at the age of 24-26 weeks (Pollari et al., 2011, Naumenko et al., 2011). Disease onset was determined by the wire-hang test where the mouse was placed hanging upside-down on a wire grid and latency to fall was recorded (Miana-Mena et al., 2005). Disease onset was determined by the inability to keep a hold on the wire grid for three minutes. The test was repeated three times per week to detect the onset age. TG and wild-type (WT) littermates were used for experiments and these littermates were randomly and equally divided into treatment groups by using GraphPad QuickCalcs.

All animal experiments were conducted according to the national regulations of the usage and welfare of laboratory animals and approved by the Animal Experiment Committee in the State Provincial Office of Southern Finland.

Functional Assessment for SCI Study

Locomotor recovery was assessed using Basso Mouse Scale (BMS) (Basso et al., 2006) by two raters blinded to the experimental groups. Mice were observed separately for 4 min in each session and a nine-point scale was used for hindlimb motor function evaluation. Motor function was assessed 24 h after injury, and then weekly for 42 days. Mice with the BMS score higher than one at 24 h after injury were excluded from the future evaluation.

Permanent Middle Cerebral Artery Occlusion

Permanent middle cerebral artery occlusion (pMCAo) was induced by anesthetizing the animals as described above. A small skin incision was made between the ear and the eye and the temporalis muscle was retracted. A small craniotomy was made, the dura excised and the middle cerebral artery (MCA) was exposed. MCA was permanently occluded by using a thermocoagulator. After surgery, the mice were let to recover from anesthesia and caged in individual cages until sacrificed at 24 hours after injury.

Determination of Lesion Size by Magnetic Resonance Imaging

Ischemic lesion sizes were assessed by magnetic resonance imaging (MRI) 24 hours post ischemia. MRI was performed in a vertical 9.4T Oxford NMR 400 magnet. Briefly, the mice were anesthetized 24 h post ischemia with isoflurane. A quadrature volume coil was used for transmission and reception. Multi-slice T2 weighted images (repetition time 3000 ms, echo time=40 ms, matrix size 128*256, Field of View 19.2 mm, slice thickness 1 mm and slices 12) were obtained with double spin-echo sequence with adiabatic refocusing pulse. The lesion volume was outlined manually (blinded) from MRI images using MATLAB-software and the lesion volume was calculated by Shuaib's indirect formula (Shuaib et al., 2002).

Functional Assessment for Stroke Study

Sensorimotor deficits were evaluated using adhesive removal test (Bouet et al., 2009). Briefly, the mouse was first taken from the home cage and adhesive patches of 6.5 mm diameter (Bel-Art Products; NJ, USA) were placed on both front paws in random order. The mouse was then placed into a cubicle box and the latencies to sensing and removal of patches from both paws were recorded. Each mouse underwent three trials and the time limit for removing the tape was set to 120 seconds. Animals were tested 3 days prior to and 3 and 5 days after ischemia. Testing and evaluation were carried out by the same person in blinded fashion.

IL-33 Treatment

In the contusion SCI study, the mice received recombinant mouse IL-33 (Biolegend, SanDiego, Calif., USA) either 7 and 3 days prior to the injury, immediately after induction of SCI and at day 4 post injury or immediately after induction of SCI and 4, 7 and 11 days post injury. The final IL-33 solution contained 0.0025% bovine serum albumin (BSA) as a carrier for IL-33. The two first injections were given at a dose of 1 µg/mouse and subsequent two injections at a dose of 0.5 µg/mouse. Control mice and sham operated animals received PBS (including 0.0025% BSA) vehicle. Mice were sacrificed 28 days after injury.

In the ALS study, mice received recombinant mouse IL-33 (Biolegend, SanDiego, Calif., USA) twice per week i. p. at the dosage of 1 µg/mouse for a month and 0.5 µg/mouse for the following weeks. IL-33 was diluted into PBS right before use. PBS vehicle injections served as controls. The treatment was started pre-symptomatically at the age of 80 days and continued until the age of 20 weeks. The mice were sacrificed at the age of 22 weeks.

In the stroke study, mice received recombinant mouse IL-33 (Biolegend, SanDiego, Calif., USA) injection (1 µg/mouse) either 7 and 3 days prior to the injury, and immediately after induction of pMCAo, or only immediately after induction of pMCAo. Control mice received PBS vehicle. Either intravenous or intraperitoneal administration was utilized.

In NCL study, mice received recombinant mouse IL-33 (Biolegend, SanDiego, Calif., USA) twice per week i. p. at the dosage of 1 µg/mouse for a total treatment time of 13 days. IL-33 was diluted into PBS right before use. PBS vehicle injections served as controls. The treatment was started at the age of 9 months Immunohistochemistry For the ALS study, the mice were anesthetized with an overdose of pentobarbital sodium (Mebunat, Orion, Espoo, Finland) and transcardially perfused with heparinized saline to remove blood from tissues. The meninges were removed from the spinal cord (SC) and the mid lumbar area was cut in half longitudinally. Tissues were post-fixed in 4% PFA for 21 h at 4° C. and prepared as paraffin-embedded sections and cut with a microtome (Leica SM 2000R, Leica Instruments GmbH, Nussloch, Germany) into 5 µm sections. The spinal cord sections were immunostained with antibody to glial fibrillary acidic protein (GFAP, Chemicon) followed by the detection under fluorescence using Alexa Fluor 568-conjugated secondary antibody (Molecular Probes, Eugene, Oreg., USA). The sections were imaged with fluorescent microscope (Olympus BX51, Olympus, N.Y., USA) and the immunopositive area was quantified using Image-Pro 6.2 software (Media cybernetics).

For the SCI study the mice were perfused with 4% paraformaldehyde (PFA). The SCs were dissected out and post-fixed in 4% PFA at 4° C. for 21 h followed by cryoprotection in 10% sucrose for 24 h and 20% sucrose for the next 24 h. A 6-mm piece of the SC centered on the lesion epicenter (or respective area in shams) was embedded in Tissue-Tek O.C.T. Compound (Sakura Finetek, Zouterwoude, the Netherlands), frozen on liquid-nitrogensupercooled isopentane and stored at −700° C. for transversal 20 µm cryostat serial sectioning (Leica Microsystems GmH, Wetzlar Germany). All histological studies were performed in a blinded fashion. Luxol Fast Blue (LFB) staining was performed as described elsewhere (Yune et al., 2007). Frozen sections were processed for immunofluorescence staining with primary antibodies against glial fibrillary acidic protein (GFAP), 1:200, (Dako, Glostrup, Denmark); ionized calcium-binding adapter molecule 1 (Iba-1), 1:250, (Wako Pure Chemical Industries, Ltd, Tokyo, Japan); Arginase-1 (N-20), 1:200, (Santa Cruz Biotechnology, Inc, Heidelberg, Germany). For Arginase-1 staining antigen retrieval was done using 0.3% sodium citrate dehydrate aqueous solution (pH 6) preheated to 92° C. (Sigma-Aldrich). Next day appropriate Alexa Fluor conjugated secondary antibody (all from Life Technologies) was applied and after washing and air-drying the sections were mounted with Vectashield mounting media with Dapi (Vector Laboratories, INC. Burlingame, Calif.) or consequentially processed for double-staining with compatible antibodies.

SC sections were photographed using a digital camera (Color View 12 or F-view; SoftImaging Systems, Munster, Germany) attached to an Olympus AX70 microscope and quantified using ImagePro Plus (Media Cybernetics, Rockville, Md.) or ImageJ (Wayne Rasband, National Institutes of Health, Bethesda, Md.) software by a researcher blinded to the treatment groups. The total transverse SC section area and myelinated area were analyzed on LFB stained sections with an interval of 200 µm. SC tissue sparing was assessed by quantifying the area covered by GFAP (Klopstein et al., 2012). Astrogliosis was assessed on high-magnification images (×40) by calculating the GFAP immunoreactivity in a $7.5 \times 10^3$ µm$^2$ area in the lateral white matter at the lesion epicenter, as well as 600 and 1200 µm rostrally and caudally and was expressed as the percentage of GFAP immunoreactivity within the selected area. Arginase-1 immunoreactivity was assessed in images from the injury epicenter, 200, 600 and 1000 µm rostrally and caudally and expressed as a percent occupied by Arginase-1 immunoreactivity within the total area of the section. For quantification of GFAP immunoreactivity images were taken from left and right sides of SC and results expressed as averages of the left and right sides at the selected distance. To assess co-localization the double-stained sections were imaged using a Zeiss LSM 700 confocal microscope (Zeiss Inc., Maple Grove, USA) with an attached digital camera (Color View 12 or F-View; Soft Imaging System, Munster, Germany) running Zen 2009 Image analysis Software (Zeiss Inc., Maple Grove, USA).

Flow Cytometry

The spleen and lymph nodes were homogenized with cell strainers to produce single cell suspension. The staining of cells for flow cytometry was performed as described (Maim et al., 2005). Briefly, nonspecific antigen binding was blocked with mouse IgG (clone MOPC-21, Sigma) and the cells were stained with fluorochrome-conjugated FITC-Ly6C (BD Bioscience), PE-CD11 b and FITC-CD4. Samples were analyzed on a FACSCalibur (BD Biosciences) equipped with a single 488 nm argon laser. Data analysis was performed using Cellquest Pro software (BD Biosciences).

Quantitative Reverse Transcription Polymerase Chain Reaction (qRT-PCR)

RNA was extracted and cDNA synthesis was performed on hippocampal brain samples as described (Kanninen et al., 2008). TaqMan gene expression assays for Arginase-1 and beta-2-microgloblin were purchased from Life Technologies and utilized according to manufacturer's instructions. Duplicate reactions were performed using the StepOne Plus using conditions recommended by the manufacturer. Delta cycle threshold (Ct) method was used for normalization of expression relative to beta-2-microglobulin.

MRI Imaging of Brain Inflammation

Brain inflammation in NCL model mice was visualized by MRI as described (Montagne et al., 2012). In brief, microparticles of iron oxide were conjugated to VCAM-1 antibodies, intravenously administered to mice and imaged with MRI 30 min later. Quantitative analyses of inflammation were performed with ImagePro software.

Example 1

SCI Model

Contusion injury at the T10 level in spinal cord is the most representative model of human clinical SCI. This injury model produces spinal cord neuronal damage and consequent motor deficits, the magnitude of which is dependent on the impact of the injury. The size of the lesion and magnitude of the motor deficits are highly reproducible and constant.

Mice undergoing SCI were given four consecutive dosages of IL-33 (Biolegend, SanDiego, Calif., USA), within 2 weeks, starting either prior to the onset of injury or after the induction of injury.

Figure 1C:
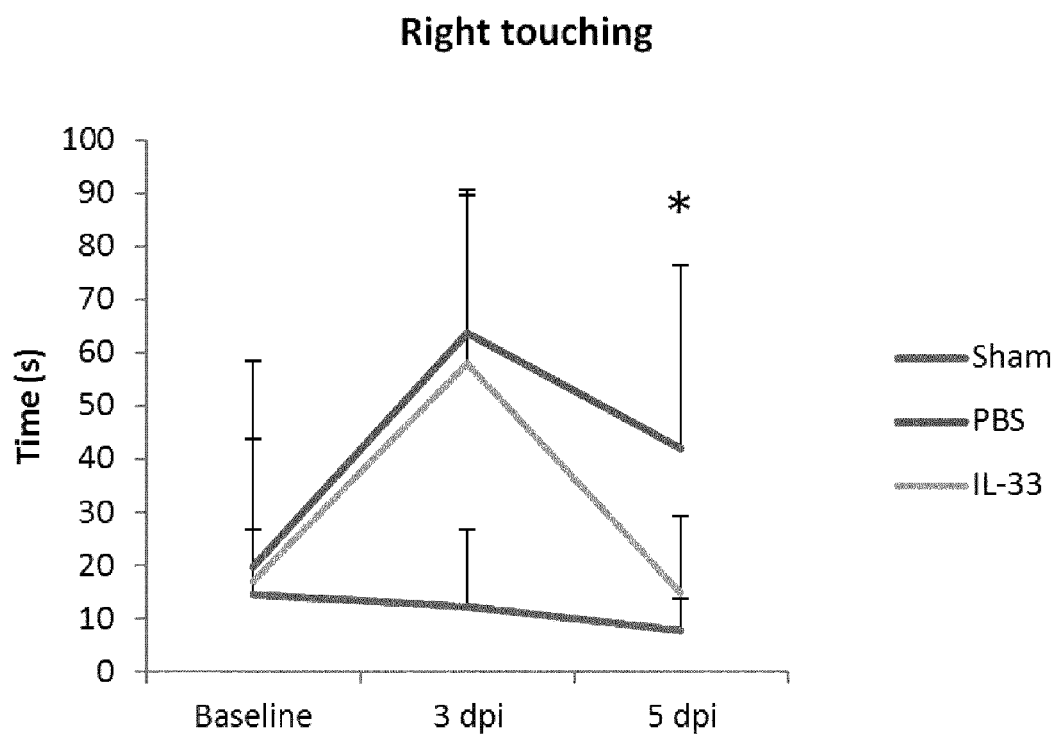
Figure 2A:
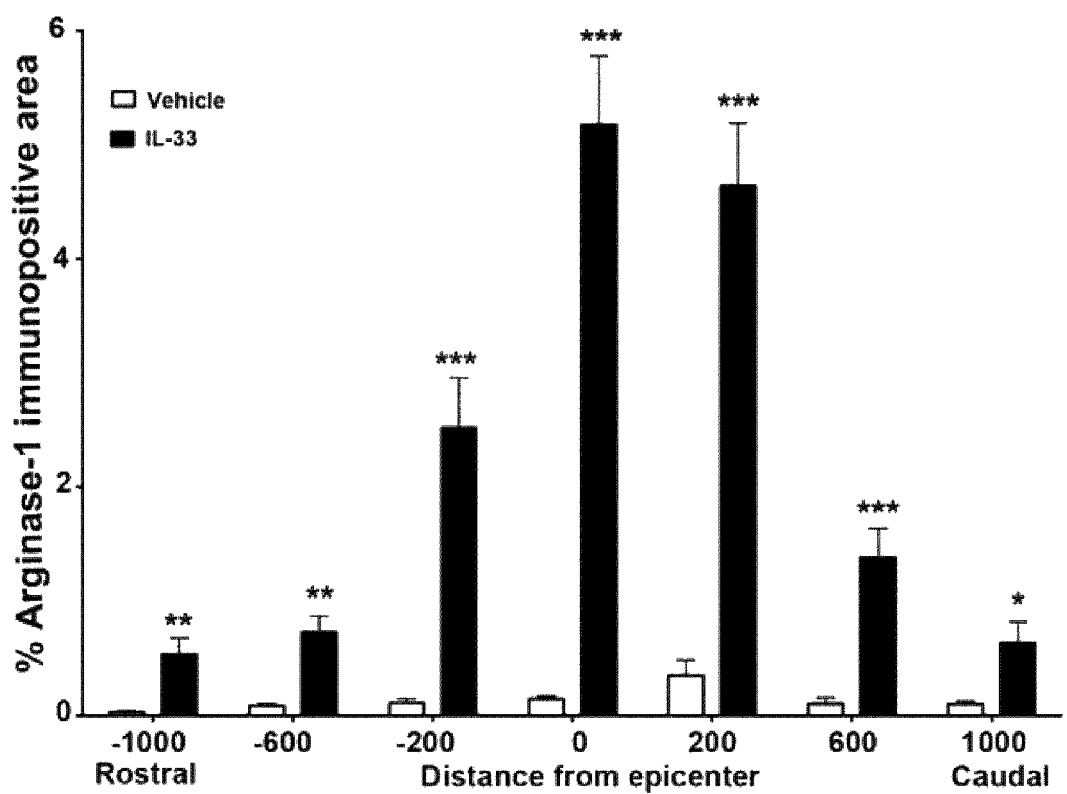
FIGS. 2A-D show that IL-33 treatment induces the expression of alternatively activated macrophages in the injured area 42 days post injury suggesting that inflammatory mileau of the injured tissue has shifted towards repair and regeneration oriented phenotype. (A) Arginase-1 immunoreactivity in vehicle and IL-33 treated groups at lesion epicenter and adjacent sections was assessed by Arginase-1 staining. (B, C) Representative images from the lesion epicenter (0 μm) showing increased arginase-1 immunoreactivity after IL-33 treatment. Scale bars=250 μm. (D) Confocal images showing double labelling for IL-33 and macrophages/microglia marker IBA-1 I in the group treated with IL-33. Scale bars=20 μm. The data are shown as mean±standard error of mean. n=8-10.*p<0.05, p<0.01, *p<0.001.
Figure 2B:
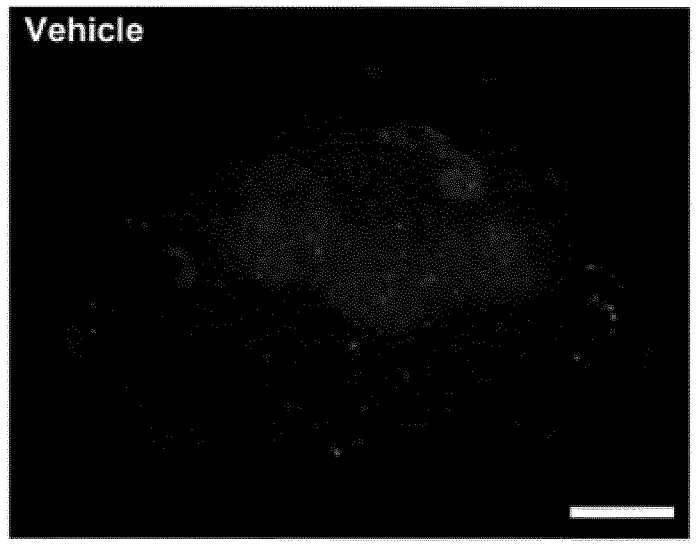
Figure 2C:
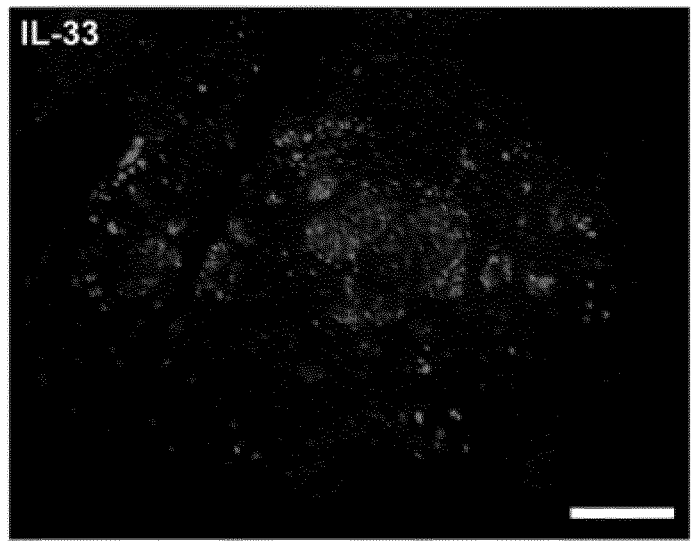
Figure 2D:
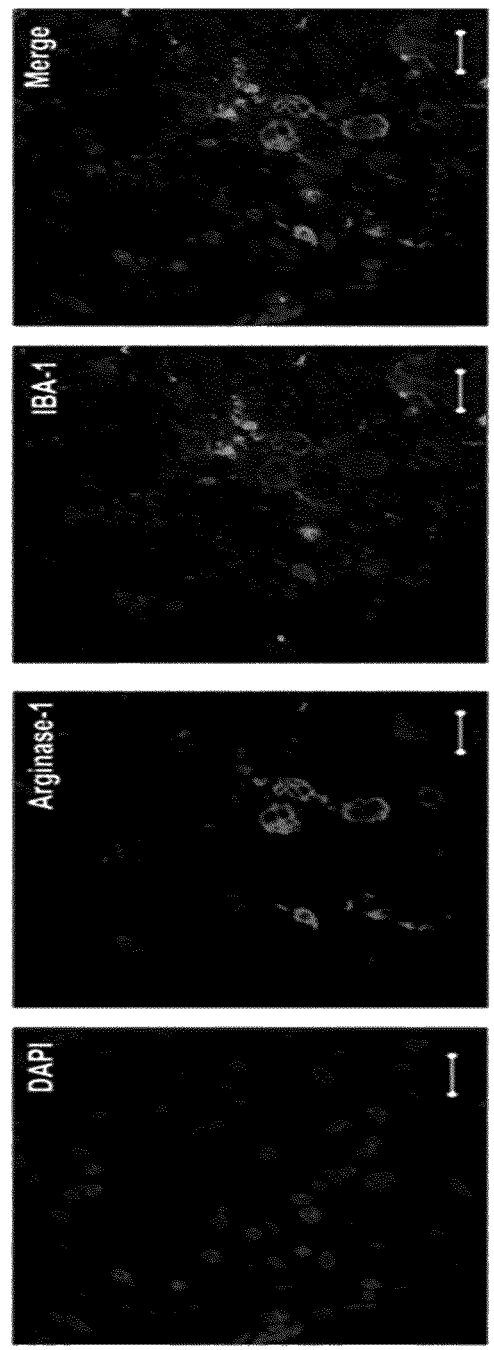

IL-33 treatment ameliorated SCI induced motor deficits in C57BL/6j mice when given both pre- and post-injury. Importantly, the improvement in Basso Mouse Scale (BMS) (Basso et al., 2006) was greater when the treatment was started after injury, making this study highly clinically relevant. (FIGS. 1A and B) Indeed, IL-33 treatment results in long functional improvement following chronic CNS condition. IL-33 treatment improved the functional recovery after ischemic insult starting at 5 days post-injury (FIG. 1C). This suggests that IL-33 treatment enhances the recovery pathways taking place in the later phases following brain injury.

Figure 3A:
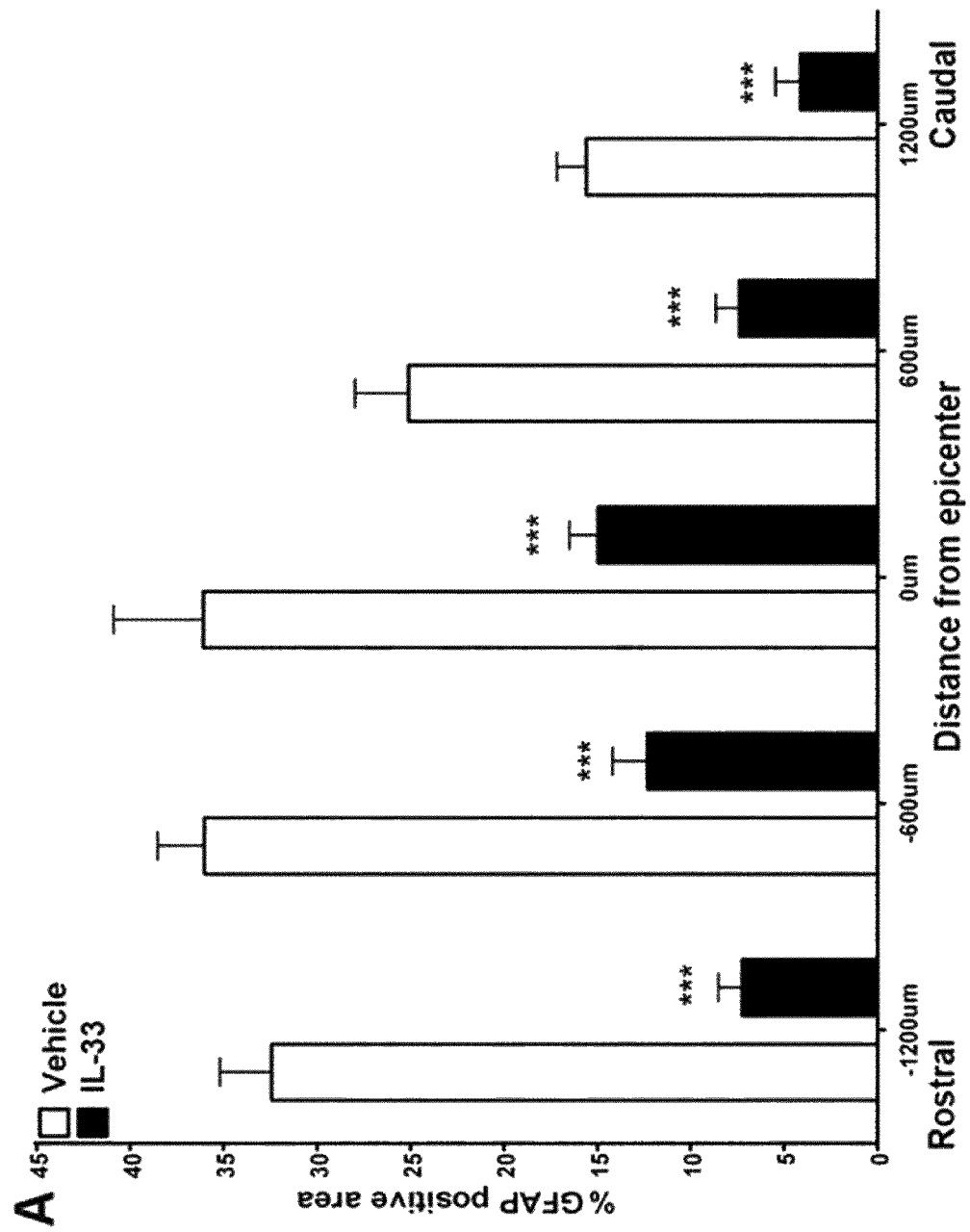
FIGS. 3A-C show that IL-33 treatment reduces astrogliosis after contusion SCI. Astrogliosis may be a hindrance of restoration of neural connectivity and endogenous repair mechanisms. (A) Astrogliosis in vehicle and IL-33 treated groups at lesion epicenter and adjacent sections was assessed by GFAP staining. (B,C) Representative images showing the degree of astrogliosis in treatment groups at distance 1200 μm rostrally to the injury epicenter. The data are shown as mean±standard error of mean. n=8-10. *p<0.05, **p<0.01. Scale bars=25 μm.
Figure 3B:
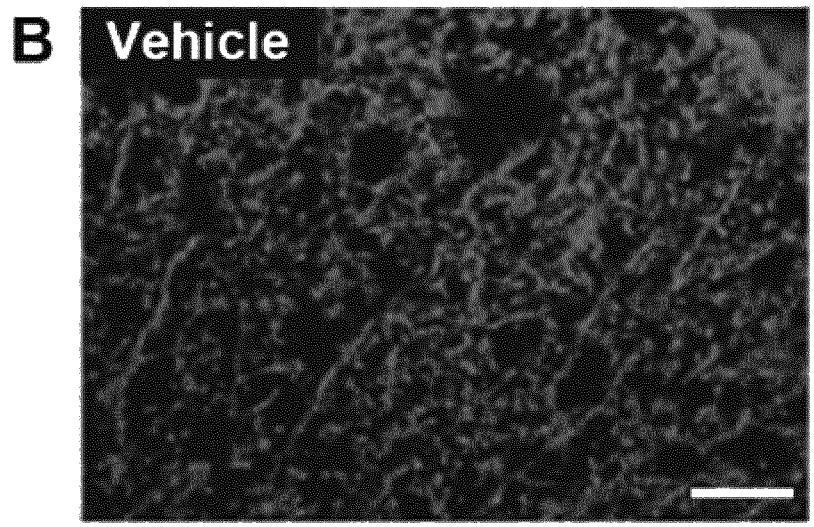
Figure 3C:
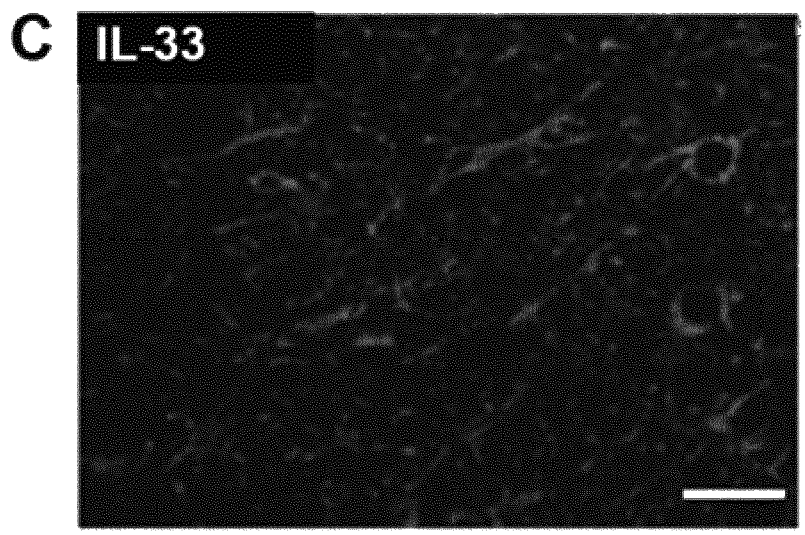
Figure 4A:
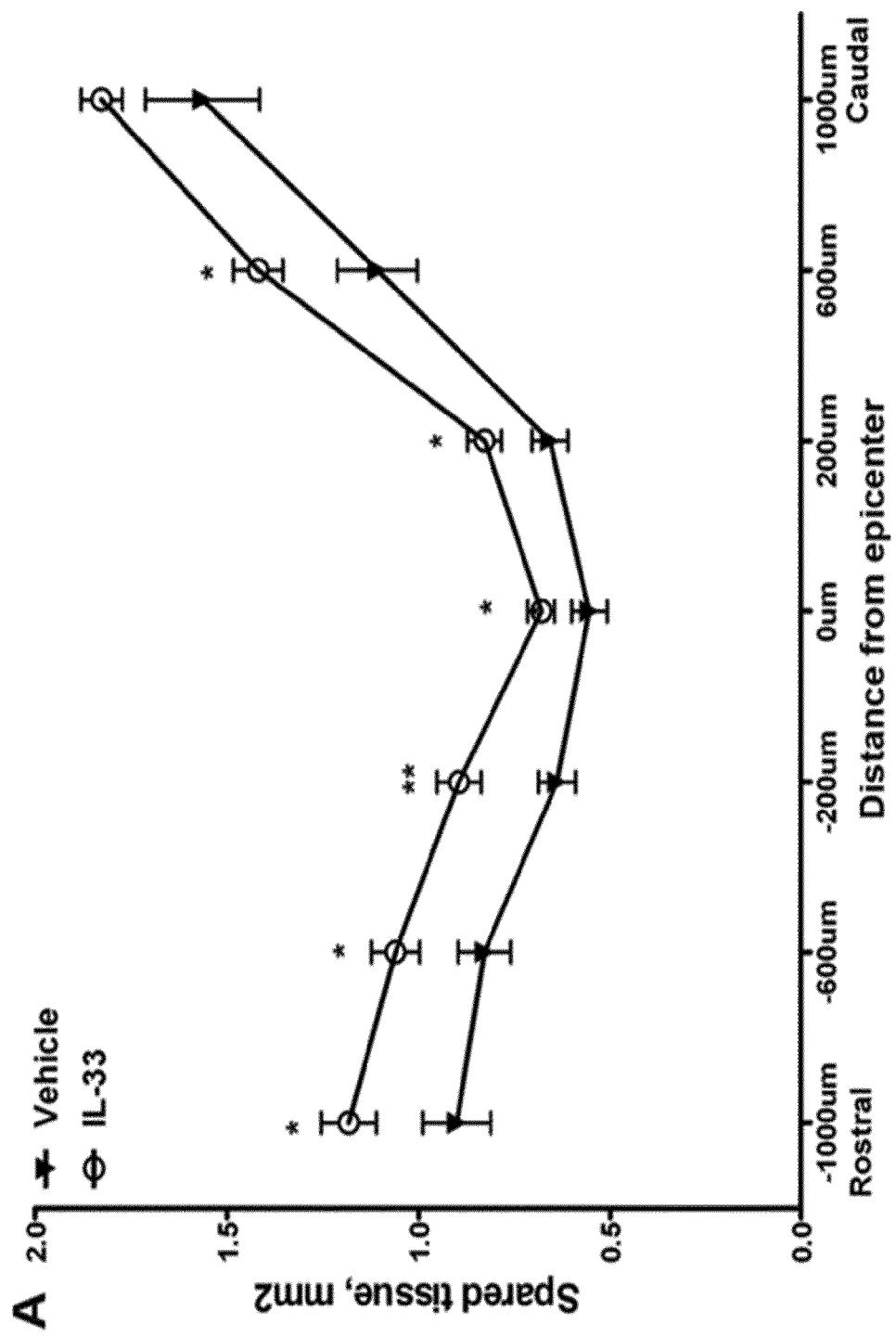
FIGS. 4A-C show that IL-33 treatment reduces tissue loss after contusion SCI. (A) Spared tissue in vehicle and IL-33 treated groups at lesion epicenter and adjacent sections was quantified as GFAP positive area. (B, C) Representative pictures show tissue sparing (GFAP positive area) in treatment groups at a distance of 1000 μm rostrally to the injury epicenter. The data are shown as mean±standard error of mean. n=8-10. *p<0.05, **p<0.01. Scale bars=250 μm.
Figure 4B:
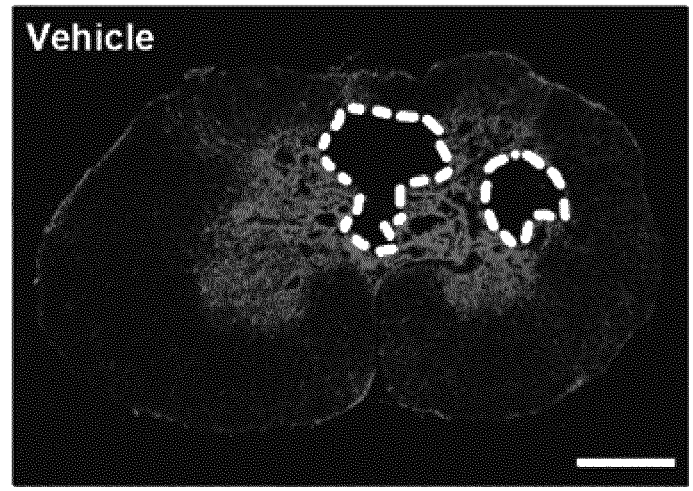
Figure 4C:
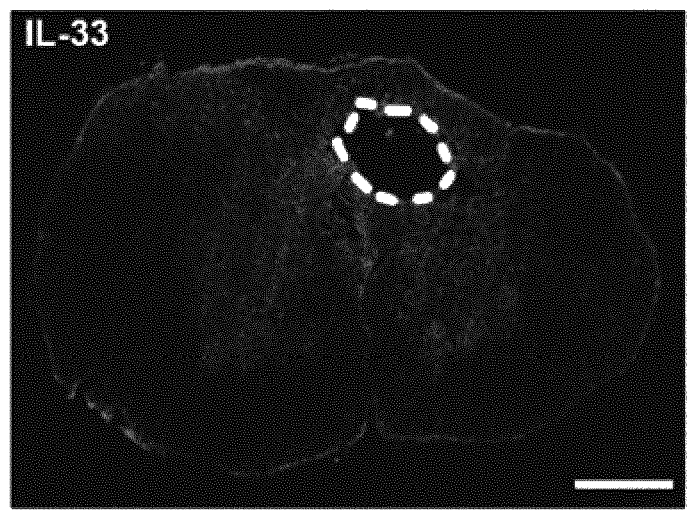
Figure 5A:
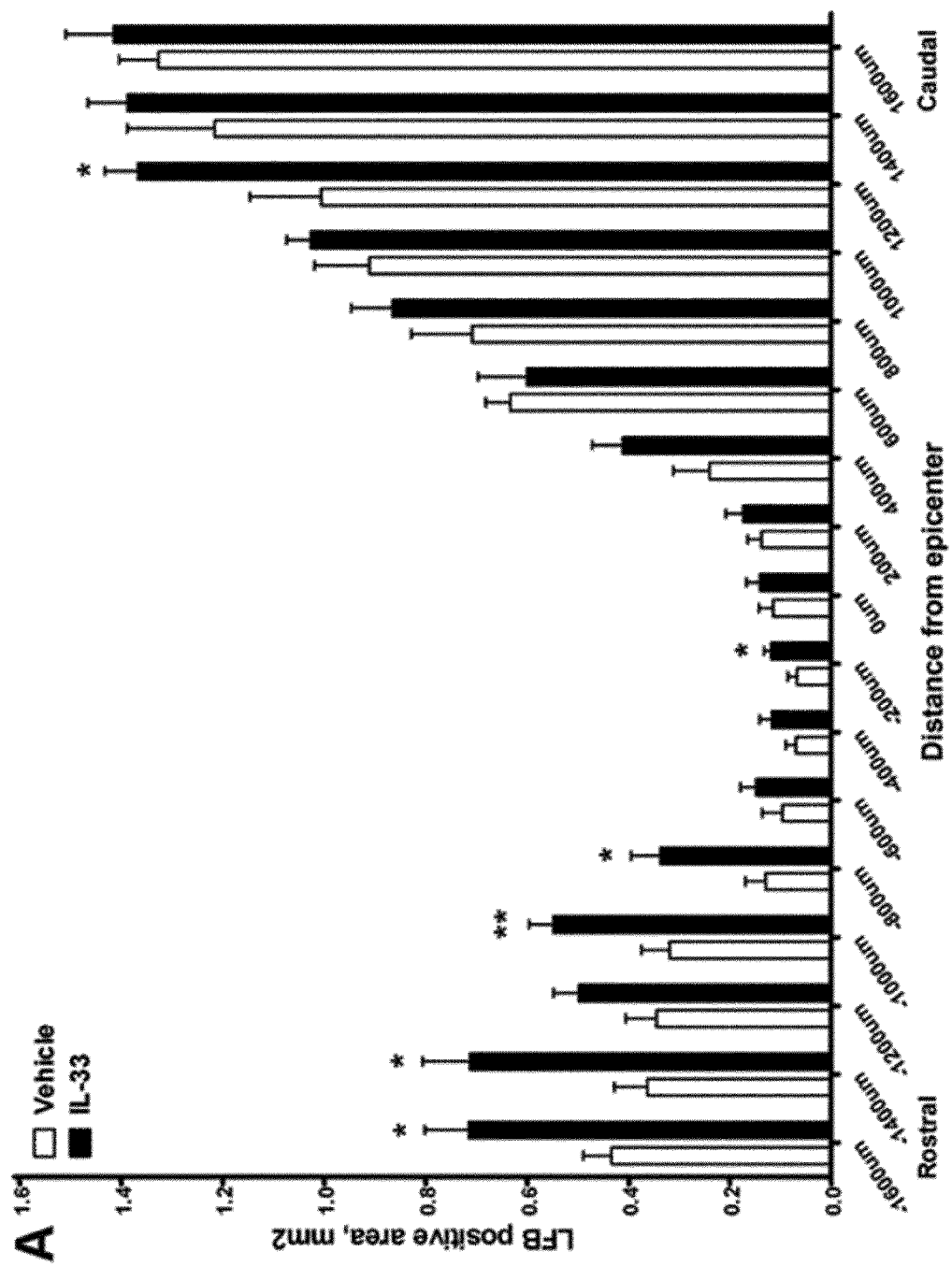
FIGS. 5A-C show that IL-33 treatment reduces demyelination after contusion SCI. (A) Spared white matter in vehicle and IL-33 treated groups at lesion epicenter and adjacent sections was quantified as LFB positive area. (B, C) Representative images show myelin sparing in treatment groups at a distance of 1000 μm rostrally to the injury epicenter. The data are shown as mean±standard error of mean. n=8-10. *p<0.05, **p<0.01. Scale bars=250 μm.
Figure 5B:
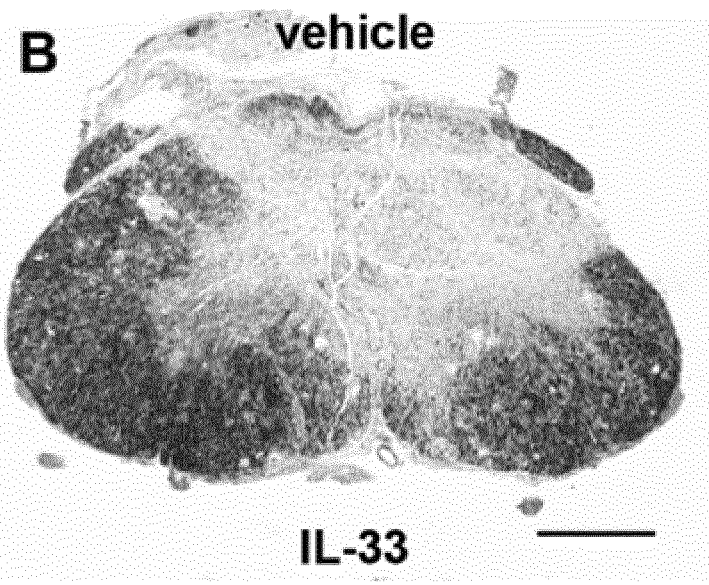
Figure 5C:
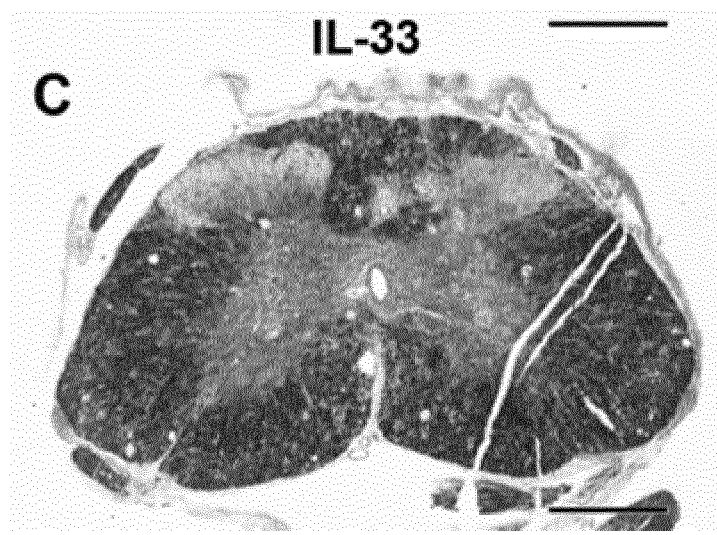

IL-33 treatment induced the expression of alternatively activated macrophages in the injured area 42 days post-injury (FIGS. 2A-D) suggesting that inflammatory mileau of the injured tissue has shifted towards repair and regeneration oriented phenotype. Also, IL-33 treatment reduced astrogliosis after contusion SCI (FIGS. 3A-C). Astrogliosis may be a hindrance of restoration of neural connectivity and endogenous repair mechanisms. Furthermore, IL-33 treatment reduced tissue loss (FIGS. 4A-C) and demyelination (FIGS. 5A-C) after contusion SCI.

Example 2

ALS Model

Identification of genetic deficits responsible for ALS has enabled the creation of precise genetic models of ALS. The G93A-SOD1 mouse strain is the most widely used model in ALS research, which leaves the enzyme activity intact. Due to the ready availability of the G93A mouse, many studies of potential drug targets and toxicity mechanisms have already been carried out in this model, and was utilized here.

Mice received recombinant mouse IL-33 (Biolegend, SanDiego, Calif., USA) twice per week with PBS vehicle controls. The treatment was started pre-symptomatically at the age of 80 days and continued until the age of 20 weeks. The mice were sacrificed at the age of 22 weeks.

Figure 6A:
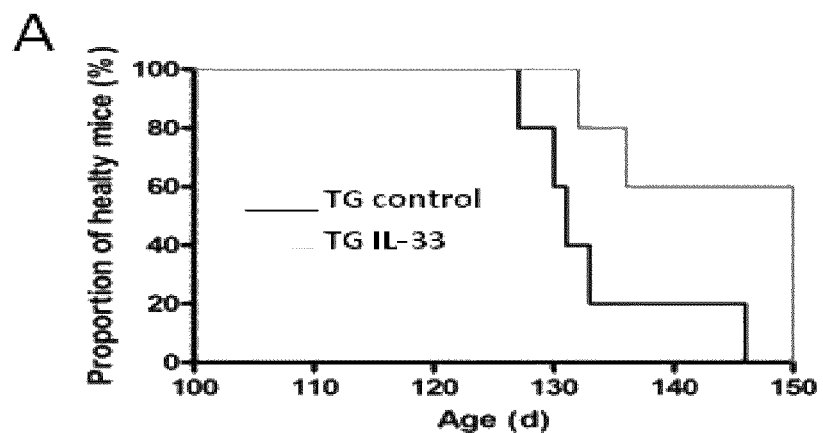
FIGS. 6A-F show that treatment of ALS transgenic mice with IL-33 significantly delays disease onset as presented by a Kaplan-Meier survival curve (A). This is associated with decreased levels of CD4+ cells in lymph nodes as analyzed by flow cytometry (B) and diminished astrocyte activity in the spinal cord ventral horn (C) as analyzed by immunohistochemical staining against glial fibrillary acidic protein (GFAP). Figures E-F represent typical examples of GFAP immunoreactivity in the ventral horn of spinal cord of WT control (D), TG vehicle treated (E) and TG IL-33 treated mouse (F). The data are shown as mean±standard error of mean. * indicates p<0.05 and ** indicates p<0.01 (repeated measures two way ANOVA with Bonferroni posthoc test).
Figure 6B:
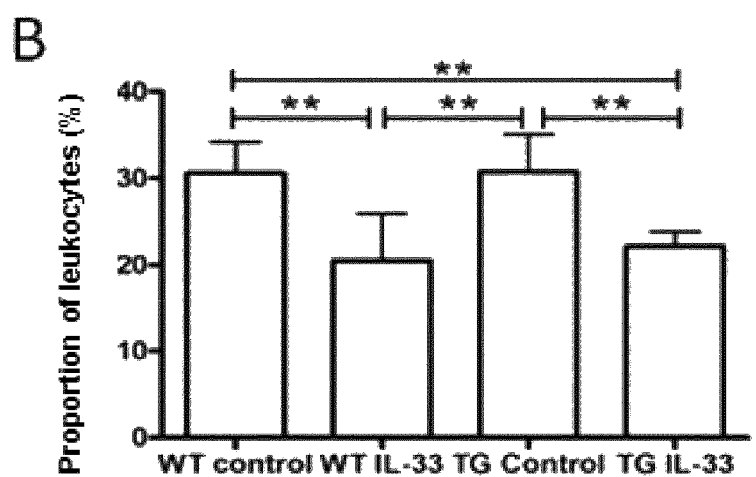
Figure 6C:
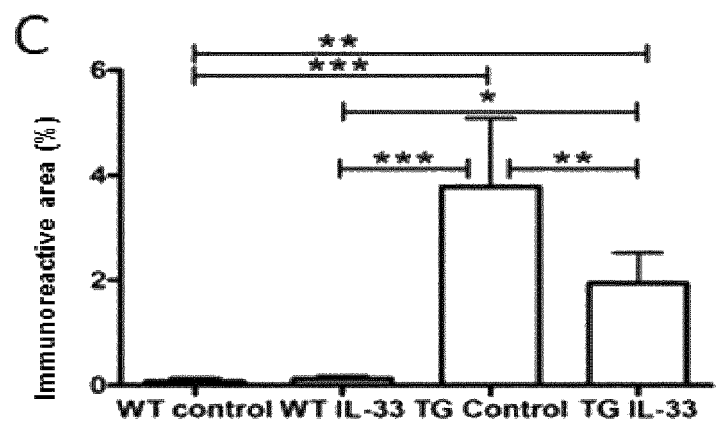
Figure 6D:
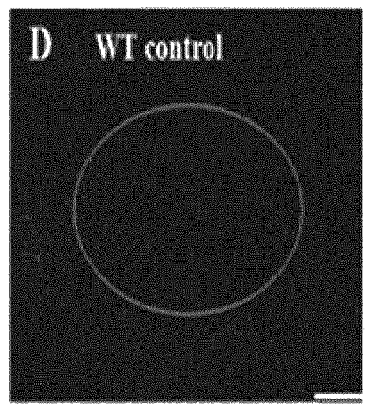
Figure 6E:
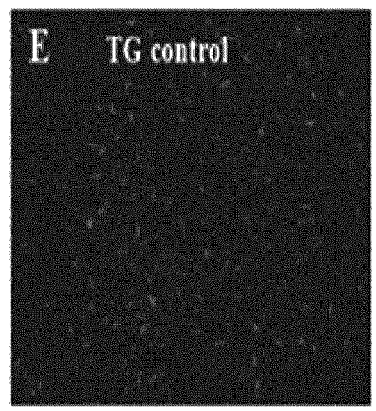
Figure 6F:
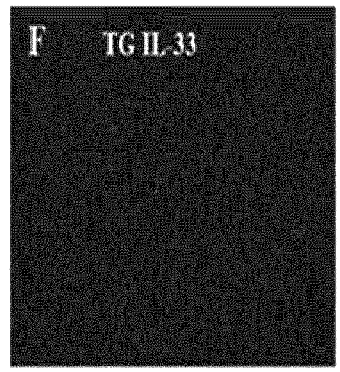

IL-33 treatment significantly delayed disease onset (FIG. 6A) compared to controls. To investigate whether IL-33 treatment had a beneficial effect on the T-cell profile in ALS, the lymphocyte populations in lymph nodes were analysed. IL-33 treatment reduced the proportion of CD4+ T-cells in the analyzed tissues (FIG. 6B). IL-33 treatment reduced astrocytic activity in the spinal cord (FIG. 6C) and hence the effect of astrocyte-derived cytokine production is probably minimal in vivo. Glial fibrillary acidic protein (GFAP) can be expressed by astrocytes. An increased number of GFAP-stained astrocytes are observed in the ventral horn of spinal cord sections from ALS patients. Immunohistochemical staining showed reduced GFAP in the IL-33 treated G93A-SOD1 mice (FIG. 6D-F).

Example 3

MCAo Model

Permanent MCA occlusion is one of the most widely used preclinical models of brain ischemia and was also utilized here. Focal pMCAo models a clinical condition in which an embolus or blood clot prevents the cerebral blood flow in a restricted brain area and the lesion is produced without re-flow. This represents a human clinical stroke in situations when the patient is not suitable for thrombolysis therapy and, due to the very limited number of patients (only 5%) suitable for tPA treatment, this model has high clinical relevance.

The mice undergoing pMCAo received i.p injections of IL-33 (Biolegend, SanDiego, Calif., USA) starting either prior to ischemia or after the induction of ischemia. The mice undergoing pMCAo received i.v injections of IL-33 (Biolegend, SanDiego, Calif., USA) starting either prior to ischemia or after the induction of ischemia. The neuronal death was determined by MRI imaging at 24 hours post ischemia.

Figure 8A:
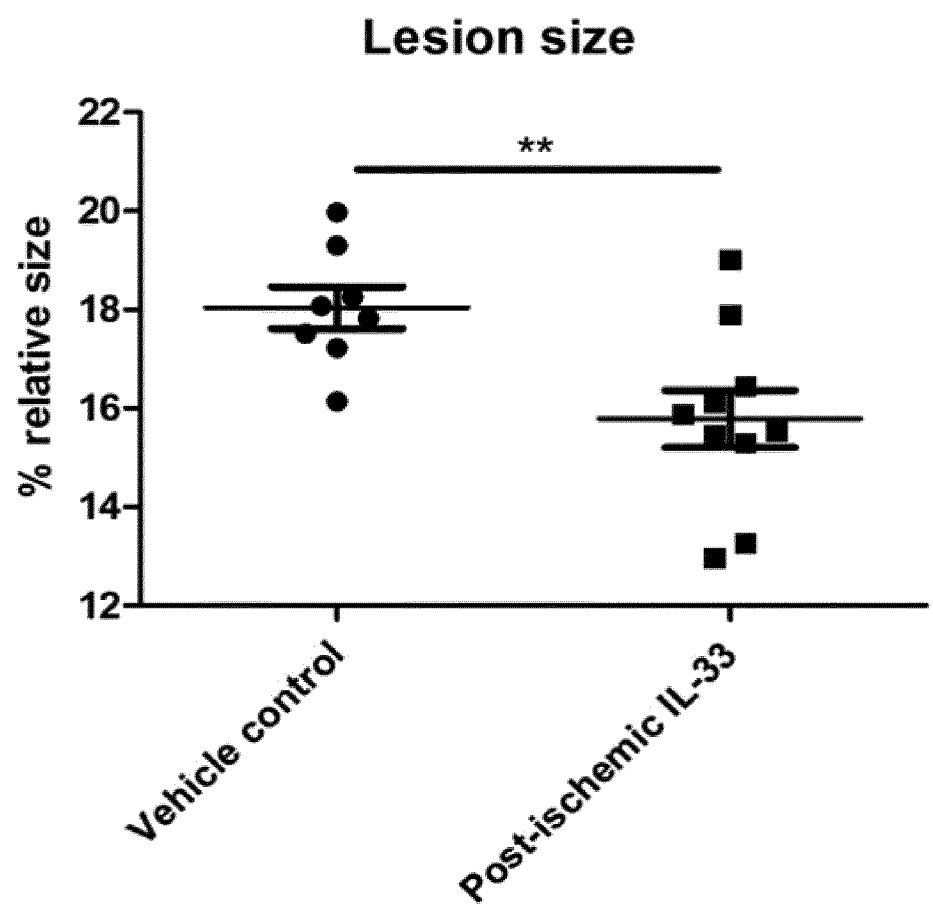
FIGS. 8A-C show that IL-33 is protective against permanent ischemia induced neuronal death when given both pre- and post-ischemic. The lesion size was imaged by MRI 24 hours after induction of ischemia. IL-33 treatment provided significant protection when given both prior to the onset of ischemia (B) and after induction of ischemia (A). IL-33 treatment is protective in pMCAO also when given as a i.v injection (C). The protection is comparable to that obtained by i.p administration of IL-33 (A). Lesion size was quantified from MRI images taken 1 day post injury. n=8-10. The data are shown as mean±standard error of mean * p<0.05.
Figure 8B:
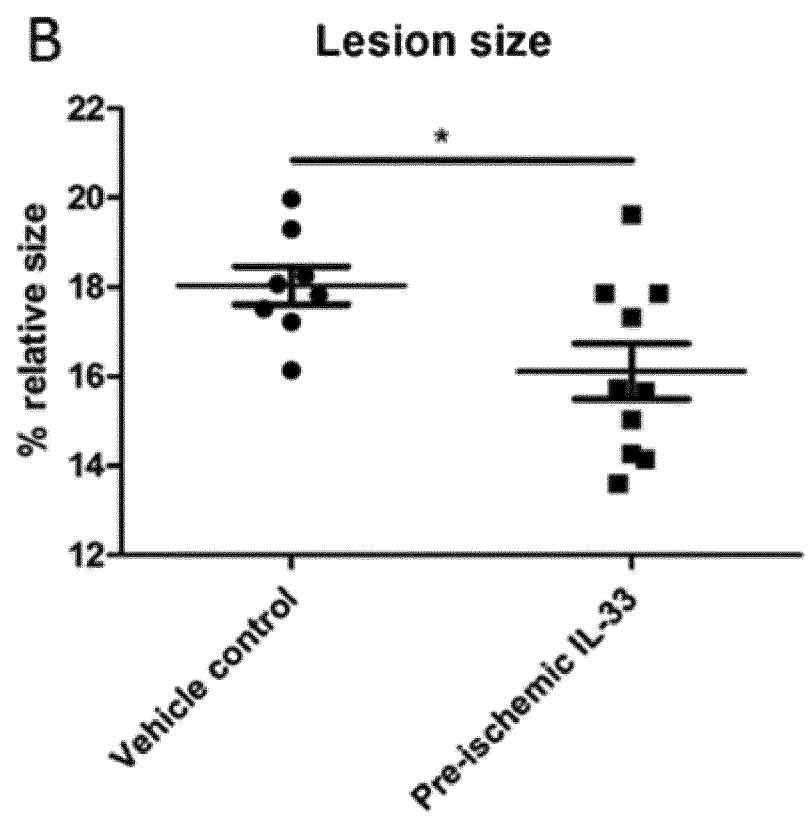
Figure 8C:
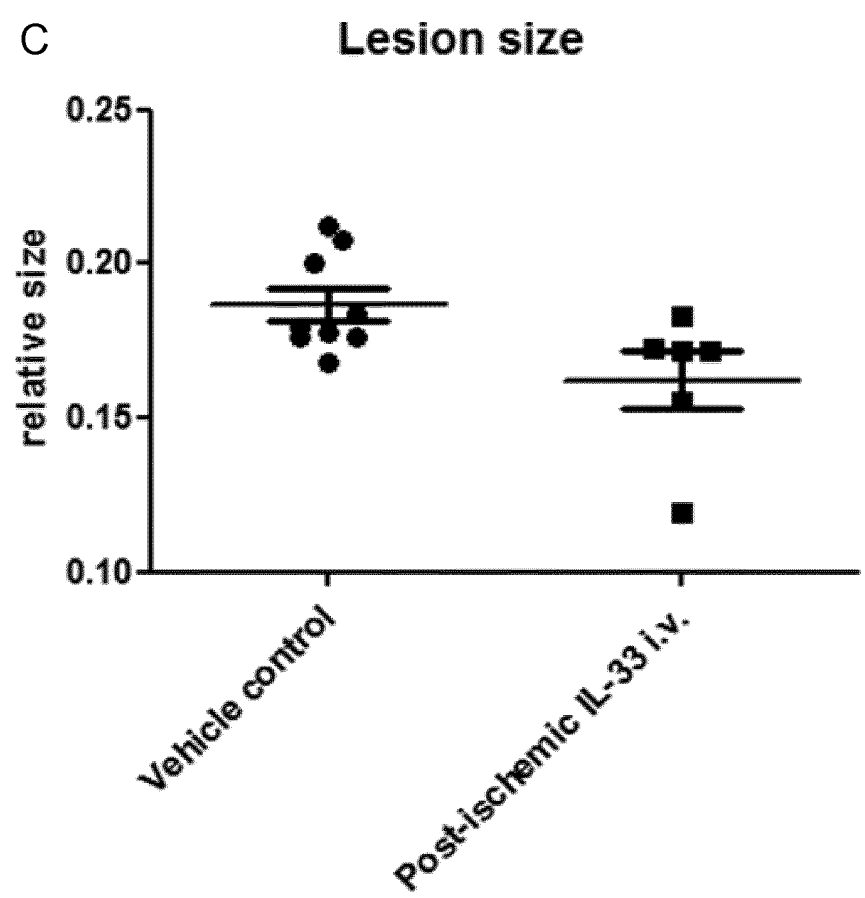

Quantification of the lesion size from MRI images showed that IL-33 treatment significantly ameliorated the ischemia induced neuronal death. The protection was significant when given both either prior to the onset of ischemia (FIG. 8B) or after the induction of ischemia (FIG. 8A). IL-33 treatment was protective when given either as a i.v injection (FIG. 8C) or i.p administration (FIG. 8A). The finding that IL-33 treatment was neuroprotective, when administered after the induction of ischemia, makes this study highly relevant to the human clinical situation.

Figure 7A:
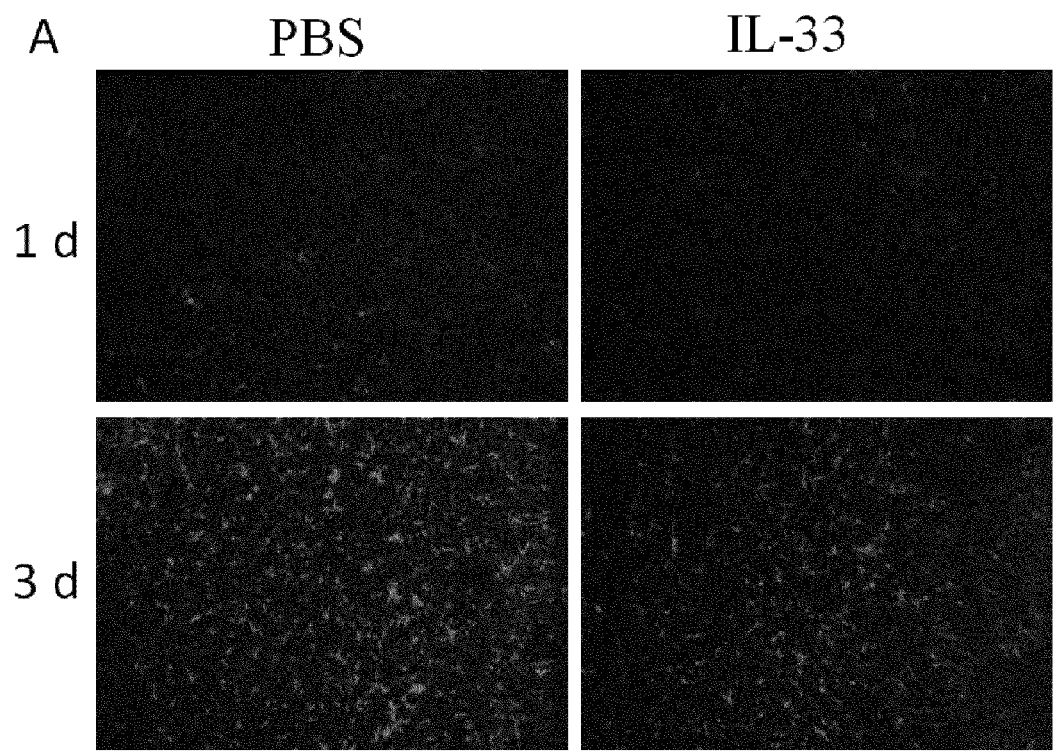
FIGS. 7A-C show the effect of IL-33 in MCAo model. IL-33 treatment significantly reduced astrocytic activation and glial scar formation after pMCAO 3 days post injury. Astrogliosis in vehicle (PCB) and IL-33 treated groups at the peri-ischemic area was assessed by GFAP staining at 1 and 3 days post injury. (A,B) In addition, IL-33 treatment reduced peripheral pro-inflammatory cytokine TNFα production in spleen (C). The data are shown as mean±standard error of mean. n=8-10. *p<0.05, **p<0.01.
Figure 7B:
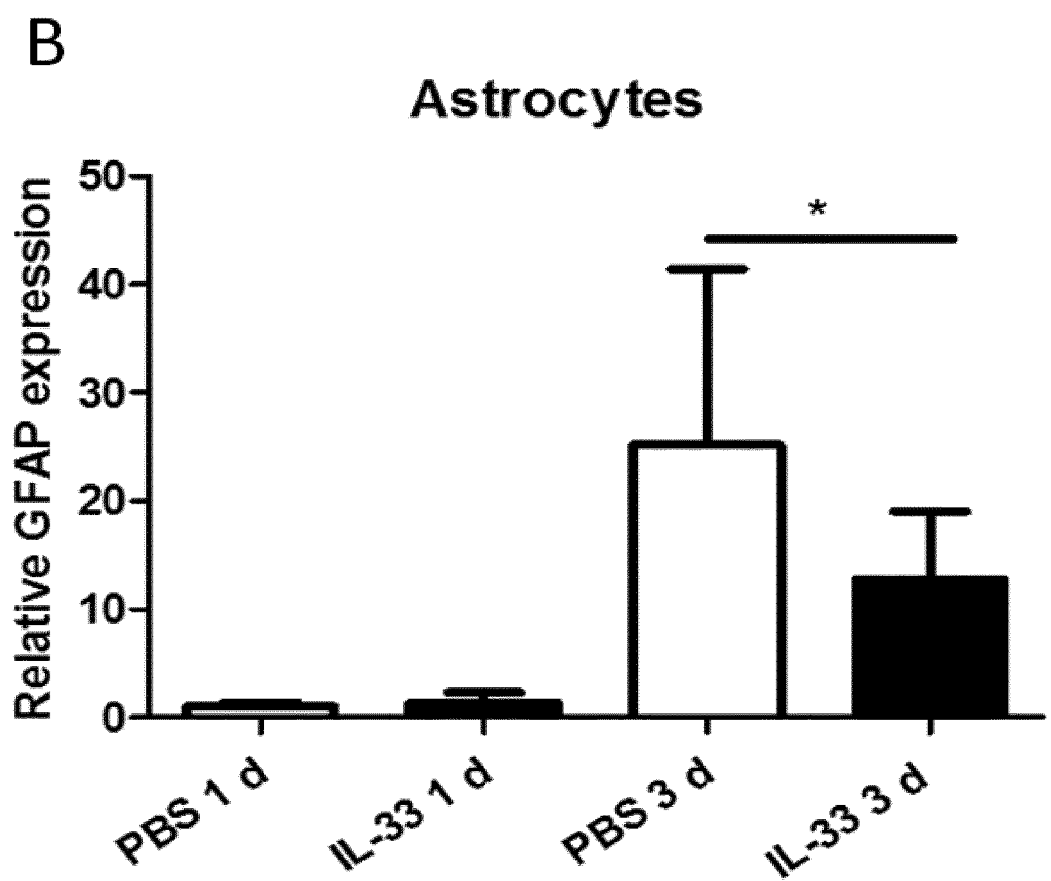
Figure 7C:
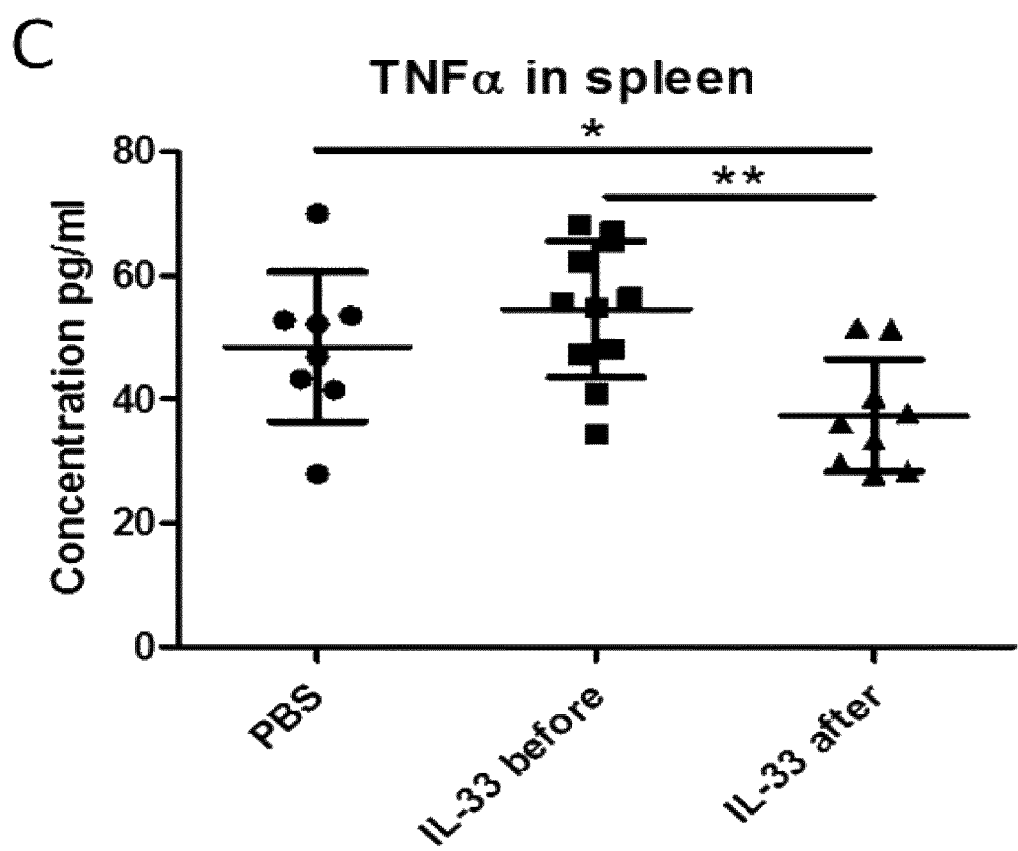

Activated astrocytes form glial scar surrounding the damaged tissue following CNS injuries. During chronic stages of the diseases this glial scar prevents the endogenous repair mechanism from taking place. IL-33 treatment significantly reduced astrocytic activation and glial scar formation after pMCAO 3 days post injury. Astrogliosis in vehicle (PBS) and IL-33 treated groups at the peri-ischemic area was assessed by GFAP staining at 1 and 3 days post injury (FIGS. 7A-B). In addition, IL-33 treatment reduced peripheral pro-inflammatory cytokine TNFα production in spleen (FIG. 7C). The data are shown as mean±standard error of mean. *p<0.05, **p<0.01.

Example 4

NCL Model

Identification of genetic deficits responsible for NCL has enabled the creation of several, precise genetic models of NCL. Here utilized was a mouse model for CLN5 (Kopra O et al.), that has been generated via the insertion of a neomycin cassette into exon 3 of the Cln5 gene, which results in a frame shift mutation with a premature stop codon, and a predicted truncated protein. This is similar to that observed in one of the human CLN5 mutations. Astrocytosis is evident by the age of four months in this mouse model.

Mice received recombinant mouse IL-33 (Biolegend, SanDiego, Calif., USA) twice per week with PBS vehicle controls. The treatment was started at the age of 9 months and continued for 13 days, after which the mice were sacrificed.

Figure 10:
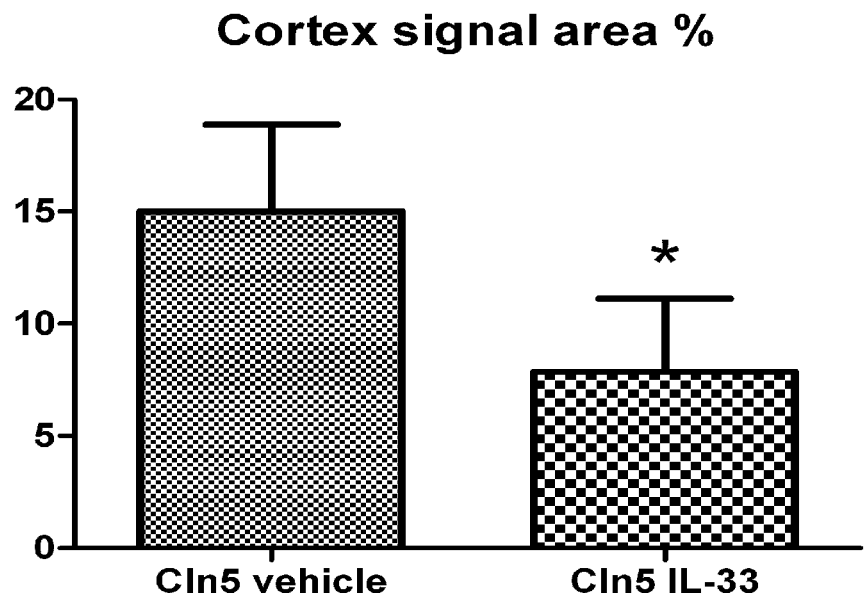
FIG. 10 shows that IL-33 treatment reduces inflammation in the cortical brain area of NCL model mice. Inflammation was quantified from MRI images after 12 days of treatment with vehicle or IL-33. Data are shown as mean±standard deviation. n=3. *p<0.05.

Brain inflammation was visualized by MRI following intravenous administration of VCAM-1 labelled MPIO particles at 12 days after beginning of treatment. Quantification of MRI images showed that IL-33 treatment significantly reduced inflammation in the brains of Cln5 mice (FIG. 10).

Figure 11:
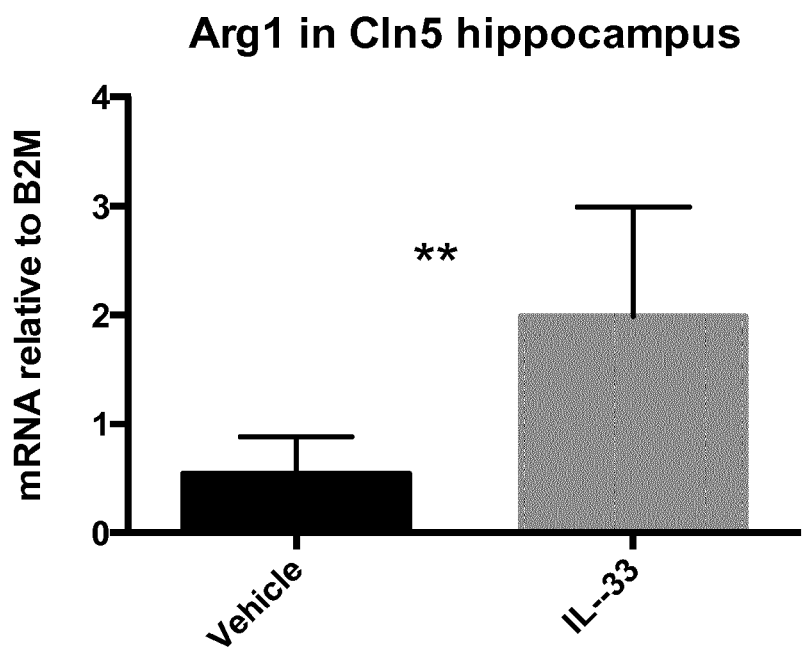
FIG. 11 shows that IL-33 treatment induces the expression of alternatively activated macrophages in the brain, suggesting that the treatment has shifted these cells towards a repair and regeneration oriented phenotype. Arginase-1 mRNA expression was measured after 13 days of treatment in vehicle and IL-33 treated NCL model mice. Data are shown as mean±standard deviation. n=6. **p<0.01.

IL-33 treatment induced the expression of alternatively activated macrophages in the brains of Cln5 mice (FIG. 11), suggesting that the inflammatory mileau of the injured tissue has shifted towards repair and regeneration oriented phenotype.

REFERENCES

Chen W.-S. et al. Inflammation and apoptosis in spinal cord injury. *Indian J. Med. Res.* 135, 287-296 (2010).
Yoshimura A. et al. Post-ischemic inflammation in the brain. *Frontiers in immunology* 3, 1-7 (2012).
Miller, A. M. et al. IL-33 reduces the development of atherosclerosis. *J. Exp. Med.* 205, 339-346 (2008).
Yasuoka S. et al. Production and functions of IL-33 in the central nervous system. *Brain research*, 1385, 8-17 (2011).
Christophi G. P. et al. Interleukin-33 upregulation in peripheral leukocytes and CNS of multiple sclerosis patients. *Clinical Immunology* 142, 308-319 (2012).
Jiang, H. et al. IL-33 attenuates EAE by suppressing IL-17 and IFN-gamma production and inducing alternatively activated macrophages. *European journal of immunology* 42, 1804-1814 (2012).
Lin C. Y. et al. Reduced levels of interleukin 33 and increased levels of soluble ST2 in subjects with amyotrophic lateral sclerosis. *Journal of neuroimmunology* 249, 93-95 (2012).
Chapuis, J. et al. Transcriptomic and genetic studies identify IL-33 as a candidate gene for Alzheimer's disease. *Molecular psychiatry* 14, 1004-1016 (2009).
Shuaib, A., Xu Wang, C., Yang, T. & Noor, R. Effects of nonpeptide V(1) vasopressin receptor antagonist SR-49059 on infarction volume and recovery of function in a focal embolic stroke model. *Stroke* 33, 3033-3037 (2002).
Pollari, E. et al. Granulocyte colony stimulating factor attenuates inflammation in a mouse model of amyotrophic lateral sclerosis. *J Neuroinflammation* 8, 74 (2011).
Naumenko, N. et al. Gender-Specific Mechanism of Synaptic Impairment and Its Prevention by GCSF in a Mouse Model of ALS. *Frontiers in Cellular Neuroscience* 5, (2011).
Miana-Mena, F. J. et al. Optimal methods to characterize the G93A mouse model of ALS. *Amyotroph. Lateral Scler. Other Motor Neuron Disord.* 6, 55-62 (2005).
Malm, T. M. et al. Bone-marrow-derived cells contribute to the recruitment of microglial cells in response to beta-amyloid deposition in APP/PS1 double transgenic Alzheimer mice. *Neurobiol. Dis.* 18, 134-142 (2005).
Nishi R A. et al. Behavioral, histological and en vivo magnetic resonance imaging assessment of graded contusion spinal cord injury in mice. *J Neurotrauma* 24, 674-89 (2007).
Bouet V. et al. The adhesive removal test: a sensitive method to assess sensorimotor deficits in mice. *Nat Protoc* 4, 1560-1564 (2009).
Basso D M, Fisher L C, Anderson A J, Jakeman L B, McTigue D M, Popovich P G. Basso Mouse Scale for locomotion detects differences in recovery after spinal cord injury in five common mouse strains. *J Neurotrauma* 5, 635-659 (2006).
Pollari E, et al. Granulocyte colony stimulating factor attenuates inflammation in a mouse model of amyotrophic lateral sclerosis. *J Neuroinflammation* 8, 74 (2011)
Naumenko N, et al. Gender-Specific Mechanism of Synaptic Impairment and Its Prevention by GCSF in a Mouse Model of ALS. Frontiers in Cellular Neuroscience [Internet]. 2011 [cited 2012 Oct. 31]; 5. Available from: http://www.frontiersin.org/Cellular Neuroscience/10.3389/fncel.2011.00026/abstract.
David S, Kroner A. Repertoire of microglial and macrophage responses after spinal cord injury. Nat Rev Neurosci 2011 Jun. 15; 12(7):388-399.
Gordon S. Alternative activation of macrophages. Nat Rev Immunol 2003 January; 3(1):23-35.
Ma J, Chen T, Mandelin J, Ceponis A, Miller N E, Hukkanen M, et al. Regulation of macrophage activation. Cell Mol Life Sci 2003 November; 60(11):2334-2346.
Kigerl K A, Gensel J C, Ankeny D P, Alexander J K, Donnelly D J, Popovich P G. Identification of two distinct macrophage subsets with divergent effects causing either neurotoxicity or regeneration in the injured mouse spinal cord. J Neurosci 2009 Oct. 28; 29(43):13435-13444.
Busch S A, Horn K P, Silver D J, Silver J. Overcoming macrophage-mediated axonal dieback following CNS injury. J Neurosci 2009 Aug. 12; 29(32):9967-9976.
Cassetta L, Cassol E, Poli G. Macrophage polarization in health and disease. ScientificWorldJournal 2011; 11:2391-2402.
David S, Kroner A. Repertoire of microglial and macrophage responses after spinal cord injury. Nat Rev Neurosci 2011 Jun. 15; 12(7):388-399.

Shechter R, Schwartz M. Harnessing monocyte-derived macrophages to contrrot central nervous system pathologies: no longer 'if' but 'how'. J Pathol 2013 January; 229(2):332-346.

Schwartz M. "Tissue-repairing" blood-derived macrophages are essential for healing of the injured spinal cord: from skin-activated macrophages to infiltrating blood-derived cells? Brain Behav Immun 2010 October; 24(7):1054-1057.

Shin T, Ahn M, Moon C, Kim S, Sim K B. Alternatively activated macrophages in spinal cord injury and remission: another mechanism for repair? Mol Neurobiol 2013 June; 47(3):1011-1019.

Guerrero A R, Uchida K, Nakajima H, Watanabe S, Nakamura M, Johnson W E, et al. Blockade of interleukin-6 signaling inhibits the classic pathway and promotes an alternative pathway of macrophage activation after spinal cord injury in mice. J Neuroinflammation 2012 Feb. 27; 9:40-2094-9-40.

Jiang M H, Chung E, Chi G F, Ahn W, Lim J E, Hong H S, et al. Substance P induces M2-type macrophages after spinal cord injury. Neuroreport 2012 Sep. 12; 23(13):786-792.

Fumagalli et al., Glia, 2013 June; 61(6):827-42.

Hu et al., Microglia/macrophage polarization dynamics reveal novel mechanism of injury expansion after focal cerebral ischemia. Stroke. 2012 November; 43(11):3063-70.

Pherson et al., 2014. In vivo molecular markers for pro-inflammatory cytokine M1 stage and resident microglia in trimethyltin-induced hippocampal injury. Neurotox Res. 2014 January; 25(1):45-56.

Kanninen K et al., 2008. Nuclear factor erythroid 2-related factor 2 protects against beta amyloid. Mol Cell Neurosci. 2008 November; 39(3):302-13.

Montagne V et al. 2012. Ultra-sensitive molecular MRI of cerebrovascular cell activation enables early detection of chronic central nervous system disorders. NeuroImage 63 (2012) 760-770.

Kopra 0 et al. A mouse model for Finnish variant late infantile neuronal ceroid lipofuscinosis, Cln5, reveals neuropathology associated with early aging. Hum Mol Genet. 2004 Dec. 1; 13(23):2893-906.

The invention claimed is:

1. A method of treating a neurodegenerative disease involving neuroinflammation in a subject, wherein the method comprises administration of IL-33 to the subject, wherein the neurodegenerative disease involving neuroinflammation is selected from the group consisting of tauopathies, Alzheimer's disease (AD), amyotrophic lateral sclerosis (ALS), spinal cord injury (SCI), and neuronal ceroid lipofuscinoses (NCL).

2. The method of claim 1, wherein the IL-33 comprises an amino acid sequence having at least 85% sequence identity with the sequence set forth in SEQ ID NO: 1 or SEQ ID NO: 3.

3. The method of claim 1, wherein the IL-33 comprises the amino acid sequence set forth in SEQ ID NO: 1 or SEQ ID NO: 3.

4. The method of claim 1, wherein the IL-33 has the amino acid sequence set forth in SEQ ID NO: 1 or SEQ ID NO: 3.

5. A method for improving or restoring neuronal function or endogenous neuronal repair mechanisms, or for enhancing endogenous neurogenesis, oligodendrogenesis, or neuronal differentiation: 1) in a subject with neurodegenerative disease involving neuroinflammation, or 2) in a subject after neurodegenerative disease involving neuroinflammation, wherein the method comprises administration of IL the subject, and wherein the neurodegenerative disease involving neuroinflammation is selected from the group consisting of tauopathies, Alzheimer's disease (AD), amyotrophic lateral sclerosis (ALS), spinal cord injury (SCI), and neuronal ceroid lipofuscinoses (NCL).

6. A method for improving or restoring neuronal function or endogenous neuronal repair mechanisms, or for enhancing endogenous neurogenesis, oligodendrogenesis, or neuronal differentiation: 1) in a subject with neurodegenerative disease involving neuroinflammation, or 2) in a subject after neurodegenerative disease involving neuroinflammation, wherein the method comprises administration of IL-33 to the subject, and wherein the neurodegenerative disease involving neuroinflammation is selected from the group consisting of Parkinson's disease, and traumatic brain injury (TBI).

* * * * *